(12) United States Patent
Fedele

(10) Patent No.: US 8,239,144 B2
(45) Date of Patent: Aug. 7, 2012

(54) UNIVERSAL REFRACTOMETER APPARATUS AND METHOD

(75) Inventor: Vincent Fedele, Harvard, MA (US)

(73) Assignee: Voice Systems Technology, Inc., Harvard, MA (US)

( * ) Notice: Subject to any disclaimer, the term of this patent is extended or adjusted under 35 U.S.C. 154(b) by 244 days.

(21) Appl. No.: 12/752,107

(22) Filed: Mar. 31, 2010

(65) Prior Publication Data

US 2011/0246091 A1 Oct. 6, 2011

(51) Int. Cl.
*G01B 5/28* (2006.01)
*G01B 5/30* (2006.01)

(52) U.S. Cl. .......... 702/35; 356/128; 356/129; 356/130; 356/131; 356/132; 356/133; 356/134; 356/135; 356/136; 356/137; 359/819; 359/820; 426/594; 426/595

(58) Field of Classification Search .................... 702/35; 356/128–137; 359/819, 820; 426/594, 595
See application file for complete search history.

(56) References Cited

U.S. PATENT DOCUMENTS

| | | | |
|---|---|---|---|
| 3,640,727 A | 2/1972 | Heusinkveld | |
| 4,988,590 A | 1/1991 | Price | |
| 5,355,211 A | 10/1994 | Thompson | |
| 5,582,717 A | 12/1996 | Di Santo | |
| 5,721,005 A | 2/1998 | Gutwein | |
| 6,034,762 A | 3/2000 | Cotton | |
| 6,808,731 B1 | 10/2004 | Gutwein | |
| 7,295,295 B2 * | 11/2007 | Lambert et al. | ............... 356/128 |
| 7,369,221 B2 | 5/2008 | Amamiya | |
| 7,492,447 B2 | 2/2009 | Nakajima | |
| 2004/0145731 A1 | 7/2004 | Nakajima | |
| 2004/0177762 A1 | 9/2004 | Gutwein | |
| 2005/0103202 A1 | 5/2005 | Rahn | |
| 2006/0196363 A1 | 9/2006 | Rahn | |
| 2008/0001105 A1 | 1/2008 | Chiarello | |
| 2008/0282897 A1 | 11/2008 | Webster | |

FOREIGN PATENT DOCUMENTS

| | | |
|---|---|---|
| DE | 10350747 A1 | 5/2004 |
| EP | 0554008 A2 | 8/1993 |
| EP | 1637055 A2 | 3/2006 |
| EP | 1875807 A1 | 1/2008 |
| GB | 2111377 A | 7/1983 |

OTHER PUBLICATIONS

Bellingham—"Refractive Index & Brix Temperature Relationship", Bellingham & Stanley Sheet (2007).

(Continued)

*Primary Examiner* — Sujoy Kundu
(74) *Attorney, Agent, or Firm* — Mark P Kahler

(57) ABSTRACT

A portable liquid design system includes a portable information handling system (IHS) that employs a liquid design application capable of operating in different modes to design different liquids such as corn syrup, espresso, coffee, soda pop and others. The portable liquid design system may include a refractometer to measure the refractive index and temperature of a liquid under test. The liquid design application may apply the measured refractive index and temperature to a 3 dimensional representation of the correlation of refractive index, temperature and concentration (% total dissolved solids) to determine a particular concentration corresponding to the measured refractive index and temperature. A single 3 dimensional scale may apply to virtually all values of interest of refractive index, temperature and concentration for a particular liquid under test.

25 Claims, 25 Drawing Sheets

OTHER PUBLICATIONS

Kernchen—"ABBEMAT High Performance Automatic Refractometers", (2003).
Madsen—Message from the President, ICUMSA News 39 (2000).
Pollach—Method of Particle Size Evaluation (2004, 2006).
Reichert—Instruction Manual—Brix Scale (2003).
GHCC—ExtractMoJo Coffee & Espresso Refractometers, George Howell Coffee Company (2008).
Adler Coffeegeek—"Measuring Coffee Strength With a Brix Meter", Downloaded from the Internet: URL:http://coffeegeek.com/forums/coffee/machines/372185?LastView+1227065615&Page+1> (retrieved on Jan. 27, 2010) (Jan. 16, 2006).
ATAG01—"Automatic Digital Refractometers RX-CX Series" (downloaded from www.atago.net/english/images/catalog/RX-alpha_e.pdf on Aug. 12, 2008).
ATAG02—"Digital Hand-held "Pocket" Refractometer PAL Special Scales" (downloaded from www.atago.net/english/products_palsp.php on Feb. 23, 2010).
BRIX—"Brix" (downloaded from http://en.wikipedia.org/wiki/Brix on Aug. 31, 2008).
BS Bellingham & Stanley RFM 81 Automatic for Sale—"Bellingham & Stanley Automatic Refractometer RFM 8" (downloaded from http://www.labx.com/v2/adsearch/Detail3.cfm?adnumb=366291 on Sep. 1, 2008).
CB Pub—"The Direct Reading Coffee Hydrometer" Publication No. 61, The Coffee Brewing Center (1970).
Cole-Parmer—"Refractometers" (downloaded from URL http://www.coleparmer.com/techinfo/techinfo.asp?htmlfile=Refractometers.htm&ID=633 on Sep. 24, 2008).
Hanson—"Refractometry: Theory, Analyzing Results" (downloaded from http://www2.ups.edu/faculty/hanson/labtechniques/refractometry/interpret.htm on Sep. 24, 2008).
Lingle—"The Basics of Brewing Coffee" Coffee Brewing Handbook, Speciality Coffee Association of America, ISBN 1-882552-03-2 (1996).
Lockhart—"The Soluble Solids in Beverage Coffee as an Index to Cup Quality" Publication No. 27, The Coffee Brewing Center (1969).
Paselk—"The Evolution of the Abbe Refractometer" (downloaded from http://www.humboldt.edu/%7Escimus/Essays/EvolAbbeRef/EvolAbbeRef.htm on Jun. 1, 2008).
Philiplaven—"Refractive index as a function of wavelength" (downloaded from http://www.philiplaven.com/p20.html on Jun. 1, 2008).
REICHERT1—"AR200 Refractometer User's Guide" (downloaded from www.reichert.com Feb. 1, 2010).
REICHERT2—"Reichert r2mini Digital Refractomer Brochure" (Oct. 2008).
REICHERT3—"r2mini Refractometer User Guide" (downloaded from www.reichert.com Feb. 1, 2010).
SCAA1—"SCAA Shop Technical Tools" (downloaded from http://www.scaa.org/shop/product_detail.asp?productid=R400300 on Sep. 19, 2008).
SCAA2—"Coffee Brewing Control Chart Brewing Ratio: Grams per Liter", Specialty Coffee Association of America (1966).
SCAA3—"Coffee Brewing Control Chart Brewing Ratio: Grams per 6.0 fl. oz. per Cup", Specialty Coffee Association of America (1966).
SCAA4—"Coffee Brewing Control Chart Brewing Ratio: Ounces per Half-Gallon", Specialty Coffee Association of America (1968).
SCAI—"SCAE Gold Cup Training Filter Brewing for Brewmaster's", Speciality Coffee Assn. of Europe, Coffee Fiesta, Antwerp (2007).
SCIENCECO—Automatic Digital Refractometer, Atago RX-007 (downloaded from http://secure.sciencecompany.com/Automatic-Digital-Refractometer-Atago-RX-007-alpha-P16117C688.aspx on Aug. 12, 2008).
TOPAC—"Brix Refractometers" (downloaded from http://www.topac.com/refractPR101.html on Aug. 31, 2008).
Pope R D—"Pulse brew and Pre-infusion", Tea & Coffee Asia, vol. 1, pp. 54-56, XP002567632 (Mar. 2008).
Thormalen—"Refractive Index of Water and its Dependence on Wavelength, Temperature, and Density", J. Phys. Chem. Ref. Data, vol. 14, No. 4, XP002567322 (1985).
PCT Search Report and Opinion—PCT/US2009/059588, International Filing Date May 10, 2009.
PCT Search Report and Opinion—PCT/US2009/059593, International Filing Date May 10, 2009.

* cited by examiner

FIG. 8D

Minimum — 860

| 17 % | 17.5 % | 18 % | 18.5 % | 19 % |

FIG. 8E

Maximum — 865

| 20 % | 20.5 % | 21 % | 21.5 % | 22 % |

FIG. 10A
DETAILED COFFEE MODE HELP INFORMATION

| Help | |
|---|---|
| Coffee Mode Help Page | |
| % EXT Output | % Extraction Yield Computed from Dose, Brew Water amounts and % TDS |
| % TDS Output | % Total Dissolved Solids Computed from refractive index and temperature as measured from instrument and entered using input sliders |
| Dose Input | Weight of ground coffee Double-TAP to convert UNITs |
| BEV Input | Amount of Brew Water in Volume or Weight Double-TAP "BW" to convert UNITs |
| nD Input | Refractive Index as measured from refractometer at 589.3 nm |
| °C Input | Temperature of sample as measured by refractometer in Deg C |

FIG. 10B

| Help | |
|---|---|
| °C Input | measured by refractometer in Deg C |
| Actions | Save or eMail measurements/recipe • Save by name with additional details • eMail via Contacts database |
| Recipes | Directory of saved measurements/ recipes • Load Recipe for immediate use • Sort by Name/Date • Edit, add details, notes, MAP geotag • Access MAPs using geotag INFO. Open in google MAPs, get walking/driving directions |
| Presets | Presets of traditional sizes and strengths, i.e. 1 Liter, 1-Gallon, English/Metric & Weight/Volume |
| Preferences | • Set Refractometer Type • Enter % TDS directly from Espresso Refractometer or nD and TEMP from any refractometer • Set Extraction Range Limits |

UNIVERSAL REFRACTOMETER APPARATUS AND METHOD

This patent application incorporates by reference in its entirety U.S. patent application Ser. No. 12/247,232, filed Oct. 8, 2010, by Fedele et al., entitled "Coffee Refractometer Method and Apparatus".

TECHNICAL FIELD OF THE INVENTION

The disclosures herein relate generally to an apparatus for measuring the index of refraction of a substance, and more particularly to an apparatus for measuring the index of refraction of a liquid under test.

BACKGROUND

A refractometer is a scientific instrument that is capable of determining the index of refraction of a liquid. Light bends when it travels from one medium into another medium due to a change of velocity of light as it passes through the interface between the media. When a light ray travelling in air enters a liquid medium, the light ray bends or changes direction by an amount dependent on the density of the liquid medium. The angle of refraction refers to the extent of this light bending phenomenon as the light exits one medium and enters another. Different liquids exhibit varying amounts of refraction according to their respective densities. For example, apple juice exhibits a different amount of refraction than orange juice because orange juice exhibits a substantially higher density than apple juice.

The index of refraction (nD or $n_S$) of a particular liquid relates to the amount of light bending that the particular liquid exhibits. Larger amounts of bending by a medium correspond to higher indexes of refraction. A liquid that exhibits a low amount of bending exhibits a lower index of refraction than a liquid that exhibits a high amount of bending. Tables are available that correlate indexes of refraction to different materials. Tables are also available that correlate indexes of refraction to different concentrations of particular liquid media at a particular temperature. For example, in the case of a corn syrup liquid medium, different indexes of refraction observed for different corn syrup samples correspond to different concentrations of corn syrup. Thus, by using a refractometer to observe the index of refraction of a particular corn syrup sample, one can determine the concentration of the particular corn syrup sample by referring to a table or scale that correlates the index of refraction to concentration at a particular fixed temperature.

It is known that index of refraction readings vary with the temperature of the liquid medium. Thus, for index of refraction readings and corresponding concentration values to be accurate, the temperature of the sample should be the same temperature for which the scale is correlated.

Refractive index measurements have been used for process control in the food industry since the 1940s. Typical measurements are usually for sugars in fruits such as melons, for orange and other juices, for sugar content in grapes for the wine industry, and many other examples. Refractometers are also useful for determining the total dissolved solids (TDS) of liquids such as coffee and espresso.

SUMMARY

Accordingly, in one embodiment a method designing a liquid under test is disclosed. The method includes providing, by a portable information handling system (IHS), at least one 3 dimensional (3D) polynomial scale of the correlation of refractive indexes, temperatures and concentrations of the liquid under test, the providing of the 3D polynomial scale being on a single 3D polynomial scale per liquid type basis. The method also includes measuring, by a refractometer, the refractive index and temperature of a liquid under test. The method further includes receiving, by the portable IHS, a refractive index measurement and temperature measurement from the refractometer for the liquid under test. The method still further includes applying, by the portable IHS, the refractive index measurement and temperature measurement to the 3D polynomial scale to determine the corresponding concentration of the liquid under test. The method also includes displaying, by the portable IHS, the concentration of the liquid under test from the applying step.

In another embodiment, a method of designing a liquid under test is disclosed that includes providing, by a refractometer, at least one 3 dimensional (3D) polynomial scale of the correlation of refractive indexes, temperatures and concentrations of the liquid under test, the providing of the 3D polynomial scale being on a single 3D polynomial scale per liquid type basis. The method also includes measuring, by the refractometer, the refractive index and temperature of a liquid under test. The method further includes receiving, by a liquid design application in the refractometer, a refractive index measurement and temperature measurement for the liquid under test. The method still further includes applying, by the liquid design application, the refractive index measurement and temperature measurement to the 3D dimensional polynomial scale to determine the corresponding concentration of the liquid under test. The method also includes displaying, by a display of the refractometer, the concentration of the liquid under test from the applying step.

In yet another embodiment, a liquid design system is disclosed for use on a liquid under test. The liquid design system includes a processor. The liquid design system also includes a display coupled to the processor. The liquid design system further includes a memory coupled to the processor, the memory being configured with a liquid design application that provides at least one 3 dimensional (3D) polynomial scale of the correlation of refractive indexes, temperatures and concentrations of the liquid under test, the providing of the 3D polynomial scale being on a single 3D polynomial scale per liquid type basis. The memory is also configured to receive, from a refractometer, a refractive index measurement and a temperature measurement for the liquid under test. The memory is further configured to apply the refractive index measurement and temperature measurement to the 3D polynomial scale to determine the corresponding concentration of the liquid under test. The memory is also configured to displays the concentration of the liquid under test.

In yet another embodiment, a liquid design system is disclosed that includes a liquid design application embedded in a processor. The liquid design system is intended for use on a liquid under test. The liquid design system includes a processor. The liquid design system also includes a display coupled to the processor. The liquid design system further includes a memory store situated in the processor, the memory store being embedded with the liquid design application. The liquid design application is configured to provide at least one 3 dimensional (3D) polynomial scale of the correlation of refractive indexes, temperatures and concentrations of the liquid under test, the providing of the 3D polynomial scale being on a single 3D polynomial scale per liquid type basis. The liquid design application is further configured to receive, from a refractometer, a refractive index measurement and a temperature measurement for the liquid under test. The liquid design application is also configured to apply the refractive index measurement and temperature measurement to the 3D polynomial scale to determine the corresponding concentration of the liquid under test. The liquid design application is also configured to display the concentration of the liquid under test.

In yet another embodiment, a computer program product is disclosed that includes a computer readable storage medium including a liquid design application. The liquid design application includes first instructions that provide at least one 3 dimensional (3D) polynomial scale of the correlation of refractive indexes, temperatures and concentrations of the liquid under test, the providing of the 3D polynomial scale being on a single 3D polynomial scale per liquid type basis. The liquid design application includes second instructions that receive, from a refractometer, a refractive index measurement and a temperature measurement for the liquid under test. The liquid design application also includes third instructions that apply the refractive index measurement and temperature measurement to the 3D polynomial scale to determine the corresponding concentration of the liquid under test. The liquid design application further includes fourth instructions that display the concentration of the liquid under test. The first, second, third and fourth instructions are stored on the computer readable storage medium.

BRIEF DESCRIPTION OF THE DRAWINGS

The appended drawings illustrate only exemplary embodiments of the invention and therefore do not limit its scope, because the inventive concepts lend themselves to other equally effective embodiments.

FIG. 8D shows a minimum value range screen of the disclosed liquid design application.

FIG. 8E shows a maximum value range screen of the disclosed liquid design application.

Figures 10C, 10D:
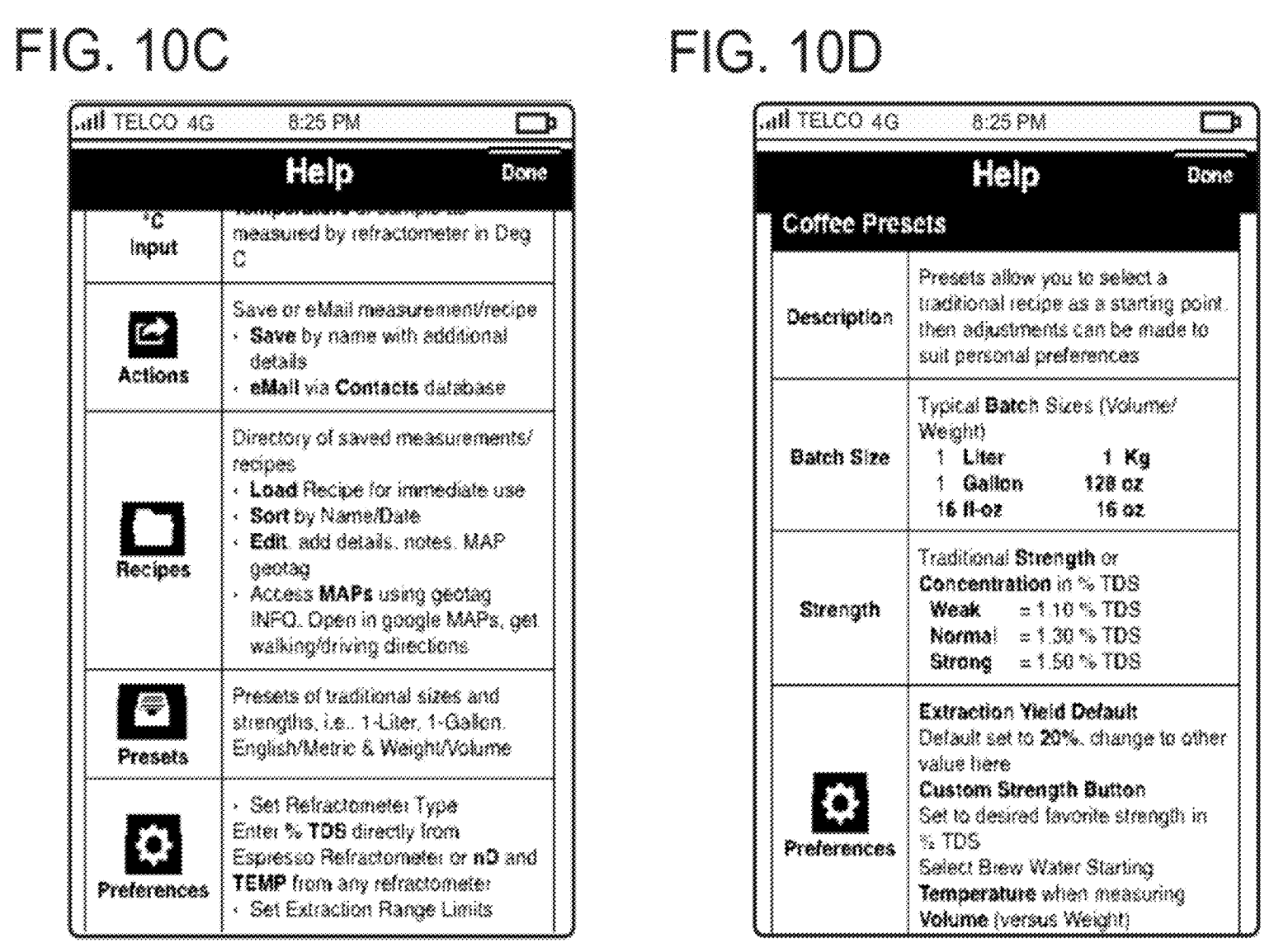

FIG. 10A-10E show different portions of a detailed coffee mode help information screen.

FIG. 12A shows the main screen of the liquid design application indicating that the extraction yield is outside of the range of interest as falling below a predetermined lower set point or trigger point of that range.

FIG. 12B shows the main screen of the liquid design application indicating that the extraction yield is outside of the range of interest as falling below a predetermined higher set point or trigger point of that range.

DETAILED DESCRIPTION

Figure 1:
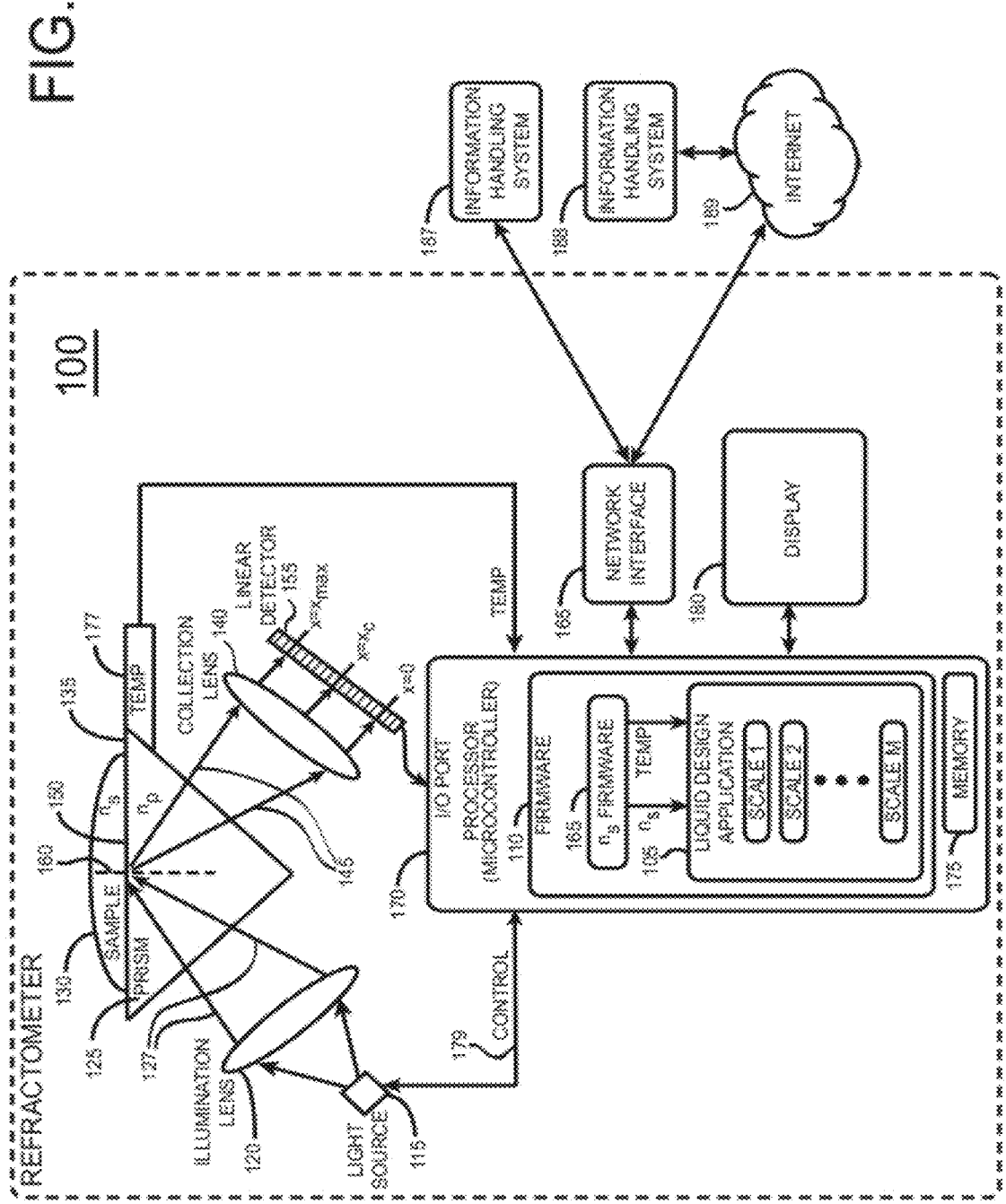
FIG. 1 is a block diagram of one embodiment of the disclosed refractometer with an embedded liquid design application.

A refractometer may have more than one scale. For example, a refractometer may include a native scale that provides the refractive index (nD) and temperature of the substance under test at a particular wavelength of light. The same refractometer may include another scale dedicated solely to a particular substance, such as a BRIX scale dedicated to measuring sucrose concentration. A BRIX scale reads percent sucrose concentration by weight in solution at a particular temperature, wherein a BRIX reading of 20.15 corresponds to 20.15% dry sucrose by weight after dehydration. BRIX is useful for determining the ripeness of fruits, vegetables and may other related food manufacturing processes. (Refractive index nD may alternatively be referred to as $n_S$ which denotes the index of refraction of a sample.)

While most refractometers may support a single scale, more expensive refractometers may support more than one scale. Refractometers that support more than one scale are typically limited to a single concentration per scale. Unfortunately, when concentration changes significantly, such a scale will not function accurately for the changed concentration. These scales are 2 dimensional (2D) scales in that they correlate two variables.

In more detail, other instruments today may include multiple scales using data inputs of refractive index and temp and concentration from users that then employ a 2D polynomial internally to determine the concentration percent over a range of refractive indexes typically at a fixed temperature. The same refractometer instrument may employ 1, 2 or more scales, wherein each scale may be used for the same liquid at a respective fixed temperature per scale.

There are two types of refractometer instruments: those with fixed temperature trays that hold the prism and sample at a temperature accurate to a few hundredths of degree C. and those that operate with a sample tray at ambient temperature. The ambient tray refractometer should be temperature corrected because there is no control of the temperature of the prism and sample liquid.

The fixed temperature tray refractometer requires a new scale to determine concentrations for each fixed temperature, using a standard 2D polynomial. Therefore, the scale for 25 degree C. would not work accurately at any other temperature. Thus, for a fixed temperature tray refractometer, a new 2D polynomial and scale should be created for each temperature at which the liquid is being measured. This occurs because dn/dt changes with temperature, wavelength (fixed) and concentration, wherein dn/dt is the change in the index of refraction over temperature.

With an ambient tray instrument, a typical embodiment will use a fixed REFERENCE temperature to create the PRIMARY scale at, for example, 25 degrees C. As long as the refractometer and sample are at 25 degrees C., the refractometer is accurate. However, as soon as the temperature changes, the concentration reported is no longer accurate. These ambient tray refractometers may use dn/dt offsets as a function of temperature to approximate or correct to the actual concentration, by using dn/dt expected over a range of temperatures. This method is an approximation by knowing the dn/dt characteristics of a liquid over a limited range of temperatures and concentrations, because the dn/dt actually changes as a function of both. The reason this approximation tends to be poor is that it is typically done by an internal lookup table, which is limited by the number of data points, range of temperature and range of concentrations that can be accommodated. An offset table often also limits the number of scales an instrument can support, due to memory limitations.

In one embodiment, the disclosed universal refractometer system and methodology employs a 3 dimensional (3D) surface plot of the correlation of refractive indexes ($n_S$) and corresponding concentrations and temperatures on a single scale using a single equation. This allows a single scale (3-D equation) to replace a very large number of multiple scales for a particular substance under test. In one embodiment, the universal refractometer system employs a 3 dimensional scale that relates refractive index ($n_S$), concentration and temperature together on single scale for a particular liquid substance under test. This single scale may be referred to as a 3D equation or a 3D surface plot that correlates with high precision the entire desired range of concentrations over the desired range of temperatures at which each nD value is known. In one embodiment that employs a correlation scale determined using a 3D surface plot, a single advanced polynomial equation can fit and apply to an entire range of refractive indexes, temperatures and concentrations. The advanced polynomial equation describes the surface of, and fits the curve of, the 3D plot of refractive indexes, temperatures and concentrations for the substance under test.

FIG. 1 shows one embodiment of a refractometer 100 that includes a liquid design application 105 for determining the concentration of a solid dissolved in a particular substance under test, i.e. a liquid under test. The refractometer 100 embeds the 3D surface plot of $n_S$, concentration and temperature, in the form of a single advanced polynomial equation, within a non-volatile firmware memory store 110 in the refractometer. This 3D surface plot, as represented by the polynomial, provides a single scale for the particular liquid under test. A single polynomial equation is fit to apply to an entire range of refractive indexes, temperatures and concentration on a single scale for the particular liquid under test. This single scale may take the place of literally dozens or more of separate scales in a stepless fashion. In the embodiment of FIG. 1, SCALE 1 is the single scale for one particular liquid under test.

Refractometer 100 includes a light source 115 such as a yellow semiconductor laser that generates 589 nm light in one embodiment. An illumination lens 120 directs the light from light source 115 toward prism 125 as shown. Prism 125 receives incident light 127 from light source 115 as shown. Prism 125 is a transparent material that exhibits an index of refraction "$n_p$". The user or other entity or apparatus places a sample 130 of the liquid under test on prism surface 135 in preparation for measurement of the index of refraction "$n_S$" that the sample 130 exhibits.

A collection lens 140 collects light 145 refracted or reflected by the prism sample interface 150 and directs that light to a linear photo detector 155. The purpose of the illumination lens 120 is to direct light from light source 115 to prism 125. More specifically, the purpose of illumination lens 115 is to form a focusing beam or cone of light incident upon the prism-sample interface 150 that ranges in angles of incidence between a minimum angle of incidence, $\theta_{min}$, and a maximum angle of incidence, $\theta_{max}$. The angle of incidence is measured relative to the normal surface 160 which is perpendicular to the prism surface 135. In one embodiment, the critical angle $q_c$ of the prism-sample interface 150 should be such that $\theta_{min} < \theta_c < \theta_{max}$. A unique property of the critical angle is that for all angles larger than $\theta_c$, 100% of the light is reflected from the interface 1034 and none transmits. For angles inside of the prism 125 that are less than $\theta_c$, some light transmits into the sample material 130 and therefore less than 100% of the light is reflected. In other words, for all rays in the beam of light generated by illumination lens 120 that are focused in the prism to an incident angle greater than the critical angle $\theta_c$, 100% of the light is reflected off of the prism-material interface 150 and propagates towards the collection lens 140 and then on to the linear detector 155 or photodetector. The light ray that is incident upon the prism-sample interface 150 at $\theta_c$ will strike the linear detector 155 at a point x=$x_c$. By analyzing the detected light levels from x=0 to x=$x_{max}$ on the detector 155, the $n_S$ firmware 165 or software of the refractometer detects the position $x_c$ since for $x_c \leq x \leq x_{max}$, the light level being substantially constant across the detector array 155. With a well-calibrated refractometer, the detector position $x_c$ is mapped back to a critical angle $\theta_c$, which from EQUATION 1 below and knowing the index of refraction of the prism $n_p$, the index of refraction $n_s$ of the sample can be determined and displayed or otherwise reported.

$$\theta_c = \arcsin(n_s/n_p) \qquad \text{EQUATION 1}$$

Therefore, in refractometer 100 the index of refraction of the prism 125 must satisfy $n_p > n_s$ for all values of $n_s$ desired to be measured in order for a critical angle $\theta_c$ to exist. Given the range of $\theta_c$ resulting from the range of $n_s$ to be measured, the illumination lens 120 arrangement is designed to include this range of angles relative to the surface normal 160 of surface 135. Similarly, the collection lens 140 is designed such that the range of angles $\theta_c$ are linearly mapped to positions x on the linear detector array 155. By way of example, for a refractometer designed to operate with a sugar solution between 0 and 10° BRIX at 20° C., one requires the ability to detect indices of refraction ranging from 1.3330 to 1.3479. Using a source with a wavelength of $\lambda_0$=589 nm and a prism made of BK7 ($n_p$=1.5167 @ $\lambda_0$), the range of critical angles to detect are $\theta_c$=61.50° to 62.71°. Choosing an Eastman Kodak (Rochester, N.Y.) linear CCD array model KLI-2113 with an array of 2098 pixels for linear detector 1035, the theoretical resolution is 7E-6 in index of refraction and 0.005° BRIX. In addition to being wavelength sensitive, the index of refraction for any material changes slightly with temperature. For water at 20° C. (68° F.) the index of refraction is 1.333 and changes by −0.0001 for every degree C.

Refractometer 100 includes a microcontroller or processor 170 with $n_S$ control firmware 165 or control software therein. Microcontroller or processor 170 includes an internal memory store 175 for storage of information and data. Alternatively, memory store 175 is located external to processor 170. Refractometer 100 also includes a temperature sensor 177 near the prism-sample interface 150 of prism 125. Temperature sensor 177 couples to an input of processor 170 to inform processor 170 of the current temperature of the prism-sample interface 150. A control line 179 couples processor 170 to light source 115 to enable processor 170 to control light source 115. Refractometer 100 also includes a display 180 to allow refractometer 100 to display measurement results such as the refractive index $n_S$, the temperature of sample 130 and the concentration of sample 130. Refractometer 100 further includes a network interface 185 that enables refractometer 100 to connect via wire or wirelessly to other information handling systems (IHSs) 187, to the Internet 189, or to other IHSs 188 via the Internet. In this manner, refractometer 100 may send measurement results to other systems.

$n_S$ firmware 165 uses the temperature from temperature sensor 177 and the information from linear detector 155 as input in conjunction with the teachings above and Equation 1 to determine the index of refraction $n_S$ for sample 130. Refractometer 100 includes a liquid design application 105 to determine the concentration of sample 130. From $n_S$ firmware 165, liquid design application 105 receives the index of refraction $n_S$ and temperature as input. Liquid design application 105 may include multiples scales such as SCALE 1, SCALE 2, . . . SCALE M, wherein M is the total number of scales that liquid design application 105 includes. In one embodiment, SCALES 1, 2, . . . M are each for different liquids types under test. For example, SCALE 1 may be for coffee; SCALE 2 may be for espresso, SCALE 3 may be for corn syrup, and so forth. Each of these scales is capable of replacing multiple scales for a particular type of substance under test. In this example, liquid design application 105 includes a SCALE 1 which is a scale that effectively stores a 3 dimensional plot of concentration values as a function of refractive indexes (nD or $n_S$) and temperature values, in the form of a polynomial equation, for the particular type of sample 130. For example, if sample 130 is a coffee type of beverage, then SCALE 1 includes a 3D surface plot of values for index of refraction, temperature and concentration of coffee, as expressed in the form of the advanced polynomial equation.

Liquid design application 105 receives the index of refraction, $n_S$, and temperature of sample 130 from $n_S$ firmware 165. Using these two values as input for the advanced polynomial equation of SCALE 1 for coffee, liquid design application 105 effectively accesses the 3D surface plot by providing these two values to the advanced polynomial equation to determine the concentration, i.e. total dissolved solids, of the coffee sample.

Processor or microcontroller 170 uses temperature sensor 177 to determine and/or set the temperature of both the prism 125 and the sample 130. Although not shown in FIG. 1, microcontroller 170 may control a resistive heater and thermo-electric cooler (e.g. a Peltier device) designed to bring the sample and prism face to a desired known and precise temperature. Because index of refraction changes with temperature and concentration and typically in a non-linear fashion, it is desirable to compensate for temperature effects. As such, in the design of the refractometer 100, it is desirable that the angles of incidences of the illumination beam at the entrance face of the prism and of the reflected beam at the exit face be minimized or at least compensated thermally because refraction at these interfaces will be a function of temperature. Likewise, the focal lengths of illumination lens 120 and collection lens 140 are a function of wavelength and to thermally compensate the temperature-dependent optical power, the lenses are preferably mounted to a mechanical mount whose thermal expansion compensates for the changes in the optical power of the lenses. Residual thermal changes to the refractometer's ability to measure index of refraction can be compensated using a lookup table based upon the readout of the temperature sensor 177 that adds a correction factor to the critical angle detected by the refractometer.

Figure 2:
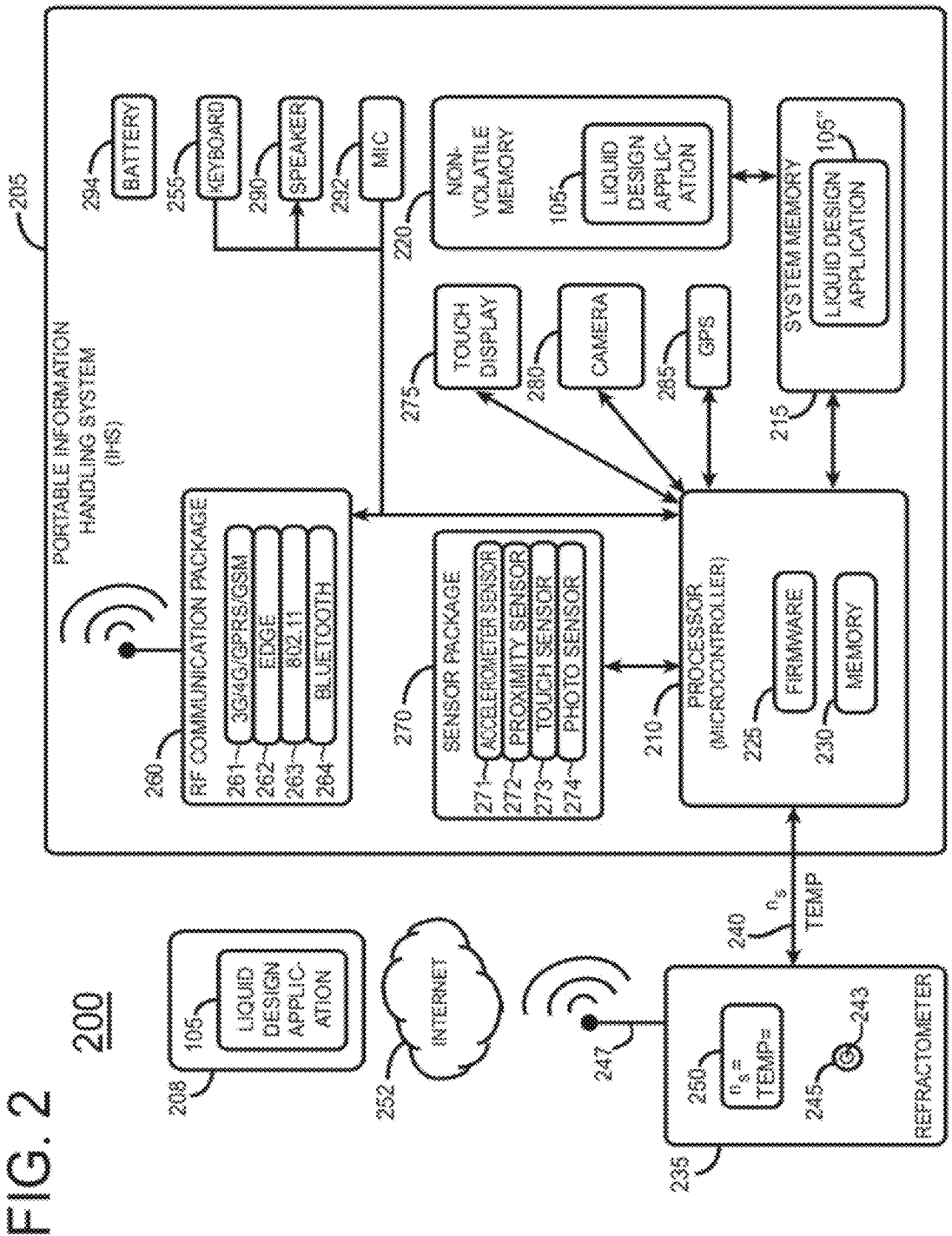
FIG. 2 is a block diagram of another embodiment of the disclosed liquid design system with a refractometer coupled to a portable IHS.

FIG. 2 shows another embodiment wherein a portable liquid design system 200 includes liquid design application 105 for determining the concentration of a solid dissolved in a particular type of liquid under test. System 200 of FIG. 2 is similar to system 100 of FIG. 1, except that liquid design application 105 is situated in a handheld or portable information handling system (IHS) 205 rather then being embedded inside the refractometer.

Portable IHS 205 may exhibit a small form factor such as a portable telephone device, smart phone device or hand-held computer. For example, portable IHS 200 may be an iPhone type IHS, a Blackberry type IHS, a Windows Phone type IHS. (iPhone is a trademark of Apple Inc. Blackberry is a trademark of Research In Motion. Windows Phone is a trademark of Microsoft.) Portable IHS 205 includes a processor or microcontroller 210 that couples to system memory 215. System memory 215 couples to a non-volatile memory 220 that loads program applications such as liquid design application 105 into system memory 215 for execution by processor 210.

Before installation on portable IHS 205, liquid design application 105 may be stored on a memory card 208 such as a flash memory card, or a standalone disc such as a CD or DVD, or in another IHS. Liquid design application 105 is a computer program product stored on a disc, SIMM card, FLASH card or other medium 208. At sometime before using liquid design application 105, a user or other entity loads or installs liquid design application 105 in non-volatile memory 220 as liquid design application 105'. To execute liquid design application 105', portable IHS 205 loads liquid design application 105' into system memory 215 as liquid design application 105". Processor or microcontroller 210 may include firmware 225 and an onboard memory 230. In one embodiment, liquid design application 105 may be installed in firmware 225. Onboard memory 230 is optional depending upon the particular implementation of portable IHS 205.

A refractometer 235 couples to processor 210 via communication bus 240 as shown. To determine the temperature and index of refraction, $n_S$, of a sample 243 of the liquid under test, the user places the liquid under test in a recessed sample receiving window 245. After completing testing of the sample, refractometer 235 sends the corresponding temperature and index of refraction results via communication bus 240 to processor 210 and system memory 215 for execution. In an embodiment wherein no wired communication bus 240 is available, refractometer 235 may alternatively transmit $n_S$ and temperature results via radio communication such as 3G/4G, GPRS/GSM, EDGE, 802.11, Bluetooth or the Internet 252 to portable IHS 205. Refractometer 235 includes an antenna 247 to facilitate radio communication of measured results. Alternatively, the user may view the measured $n_S$ and temperature results on refractometer display 250 and manually input those results into portable IHS 105 via keyboard 255. Using the measured $n_S$ and temperature results as input, liquid design application 105" determines the corresponding concentration of the liquid under test in substantially the same manner as described in the above discussion of liquid design application 105 of FIG. 1. In a manner similar to that described in reference to FIG. 1, liquid design application 105 may include multiple scales such as SCALE 1, SCALE 2 . . . SCALE M (not shown in FIG. 2).

Portable IHS 205 further includes an RF communication package 260 that includes a 3G/4G/GPRS/GSM phone communication module 261, and EDGE phone communication module 262, an IEEE 802.11 network communication module 263 and a Bluetooth local communication module 264. RF communication package 260 couples to processor or microcontroller 210. Portable IHS 205 includes a sensor package 270 that includes an accelerometer sensor 271, a proximity sensor 272, a touch sensor 273 and a photo sensor 274. Sensor package 270 couples to processor 210. Both a touch sensitive display 275 and a digital camera 280 couple to processor 210 as shown. A global positioning system (GPS) module 285 also couples to processor 210 to provide position information thereto. A speaker 290 and a microphone 292 operatively couple to processor 210 to provide audio I/O capabilities to portable IHS 205. A battery operatively couples to the various blocks of portable IHS 205 (connection not shown) to provide power to the components thereof.

Portable IHS 205 processes, transfers, communicates, modifies, stores or otherwise handles information in digital form, analog form or other form. While FIG. 2 shows one IHS that employs processor 210, the IHS may take many forms. For example, IHS 205 may take the form of a portable, laptop, notebook, netbook or other form factor computer or data processing system. IHS 205 may take other form factors such as a gaming device, a personal digital assistant (PDA), a handheld computing device, a portable telephone device, a communication device or other devices that include a processor and memory. Liquid design application 105 will also execute on a desktop, server or fixed IHS.

FIGS. 3-14 show exemplary screen captures of the display 275 as the user employs system 200 to determine the index of refraction and temperature of sample 245 and the corresponding concentration that correlates to the determined index of refraction and temperature. As the user operates system 200, liquid design application 105 executes to produce these representative screen captures.

Figure 3:
FIG. 3 shows an initialization screen that the liquid design application generates after the liquid design application launches.
Figure 4:
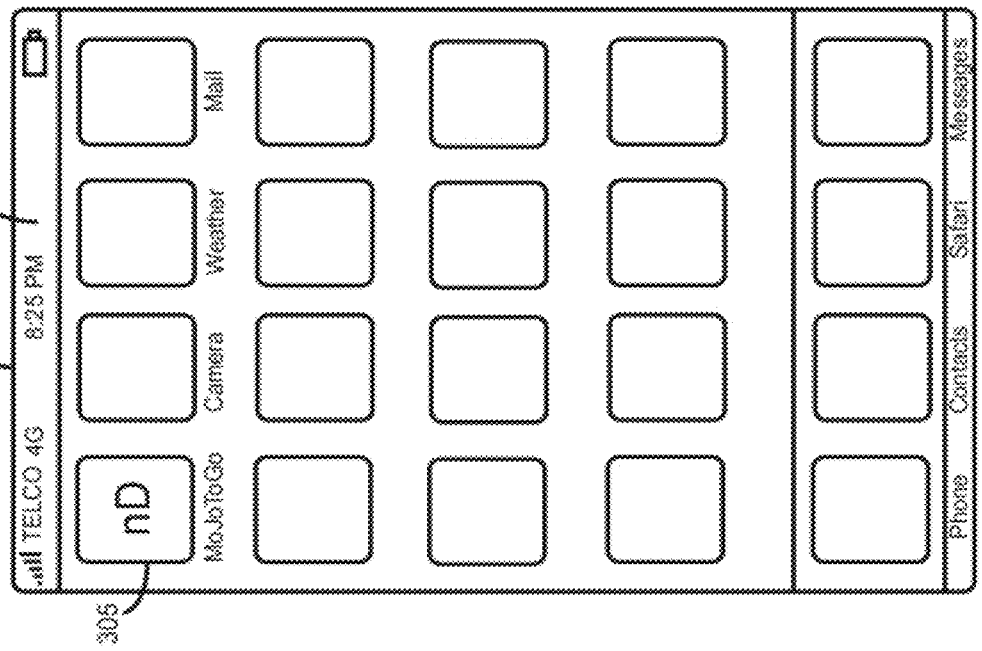
FIG. 4 shows a splash screen for the disclosed liquid design application.

FIG. 3 shows an initialization screen 301 on touch display 275 that appears after the user turns on portable IHS 205. Initialization screen 301 includes rows of icons, each icon representing a respective user application that the user may select by touching the icon for the desired application. For example, the first row of initialization screen 301 includes a "MoJoToGo-nD" icon 305 that the user may select to cause IHS 205 to launch and execute liquid design application 105. FIG. 4 shows a representative splash screen 401 that appears on display 275 when the user selects icon 305.

Figure 5:
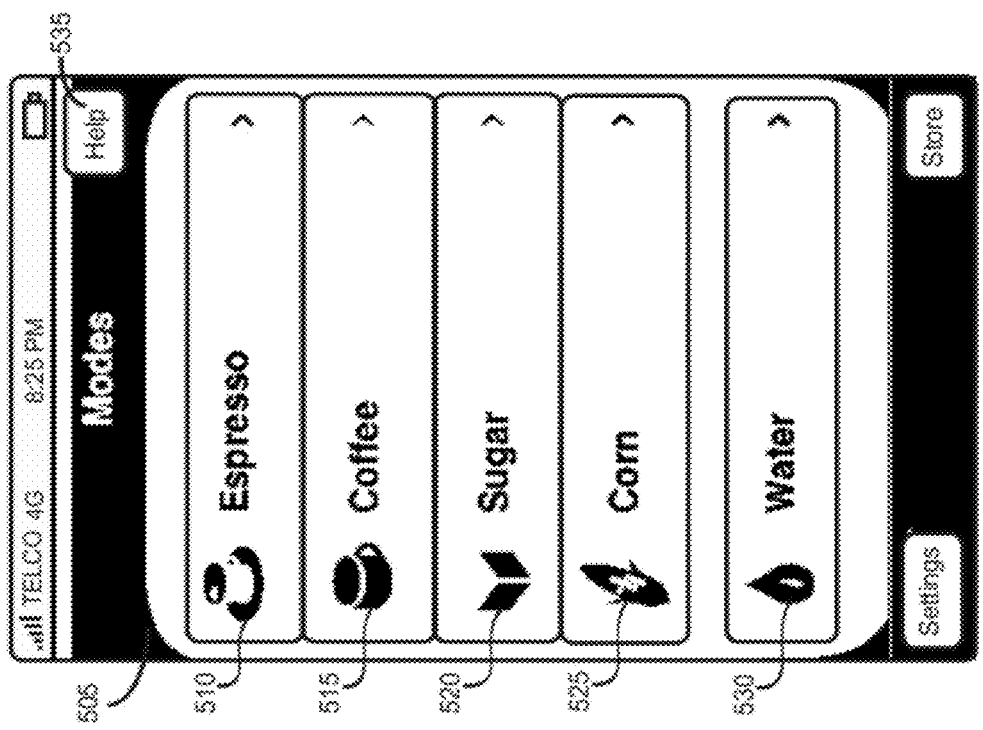
FIG. 5 shows a mode selection screen of the disclosed liquid design application

FIG. 5 shows the mode selection screen 505 that liquid design application 105 presents to the user on display 275 immediately after displaying splash screen 401. Mode selection screen 505 includes multiple modes, for example espresso mode represented by espresso icon 510, coffee mode presented by coffee icon 515, sugar mode represented by sugar icon 520, corn syrup mode represented by corn icon 525 and water mode represented by a water icon 530. To select any one of these modes, the user touches the respective icon for that mode. In response to such icon touching, liquid design application 105 enters the selected mode, for example, espresso mode if the user touched espresso mode icon 510.

Figure 6A:
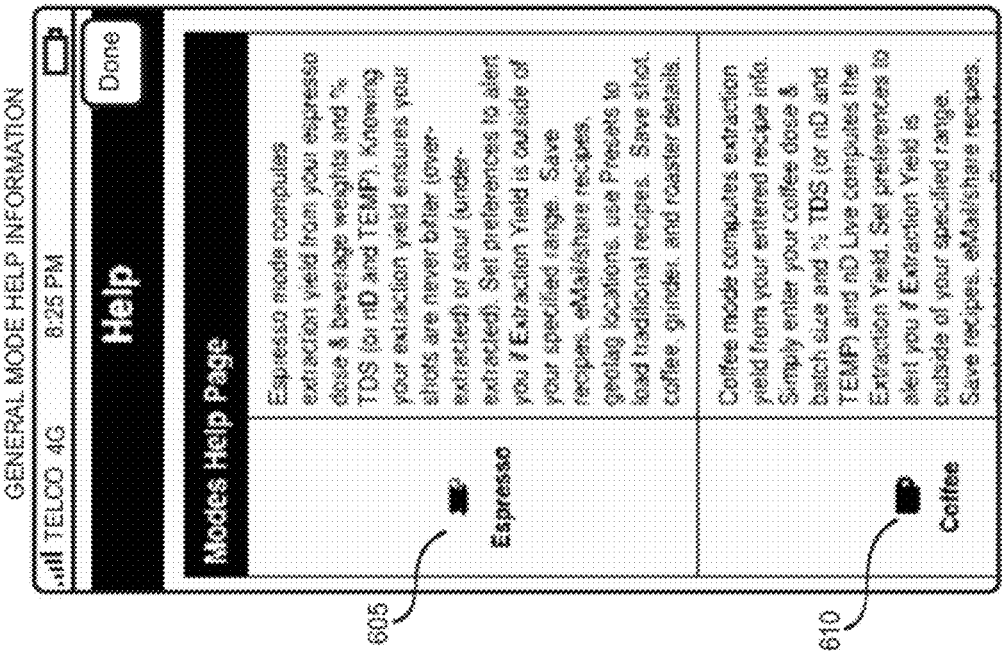
FIG. 6A-6C show representative mode help screens from the disclosed liquid design application.
Figure 6B:
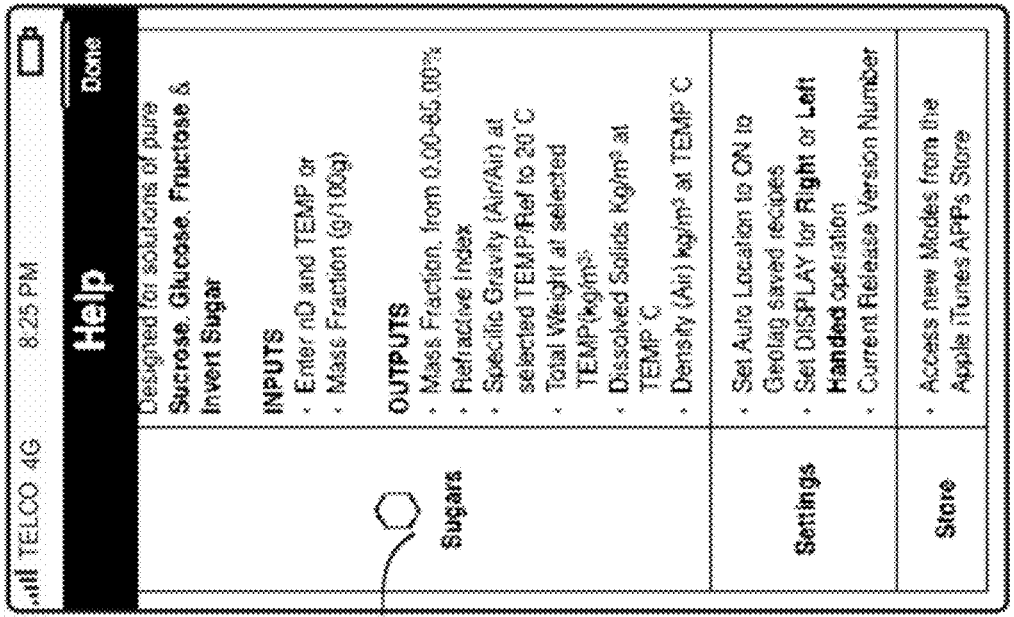
Figure 6C:
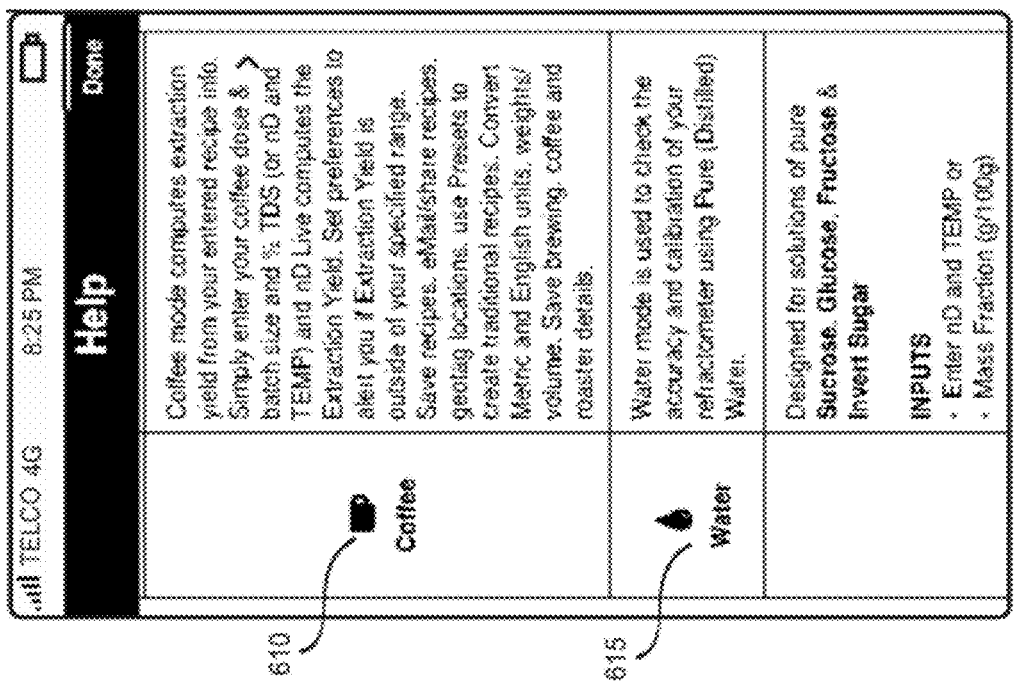

To obtain general information regarding the modes of portable IHS 205, the user touches help button 535 to select general mode information. FIGS. 6A-6C together show espresso mode help information 605, coffee mode help information 610, water mode help information 615, and sugar mode help information 620. The user may scroll through the various different help screens for multiple installed modes by touching the screen and gesturing up or down. The help screens of FIGS. 6A-6C are general mode help screens which are to be distinguished from the more detailed specific mode help screens described below with reference to FIGS. 10A-10E.

Figure 7:
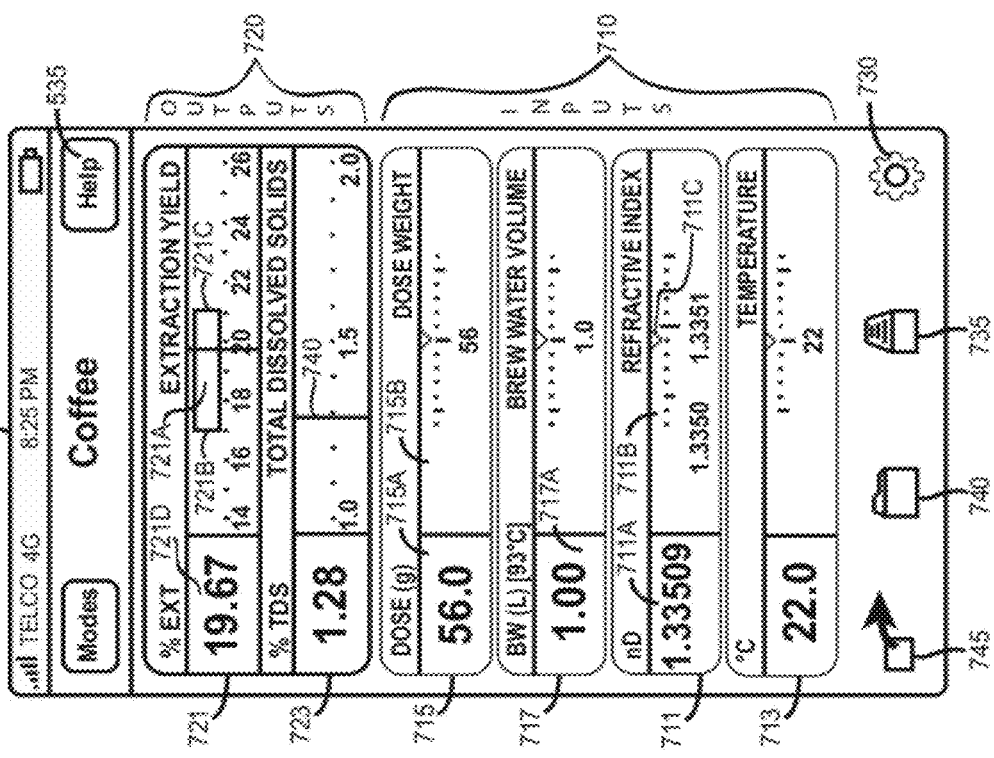
FIG. 7 shows one of many liquid modes that the user may install for use with the disclosed liquid design application.

FIG. 7 shows one of many liquid modes that a user may install in portable IHS 205 for use with liquid design application 105. More particularly, FIG. 7 shows a representative coffee main mode screen 700 that appears when the user selects coffee icon 515 on mode selection screen 505 of FIG. 5. Main mode screen 700 includes an input section 710 and an output section 720.

Input section 705 includes a refractive index input dial 711 and a temperature index input dial 713 that receive refractive index information and temperature information, respectively, directly or indirectly from refractometer 235. When a user places a liquid sample in refractometer 235, the refractometer may transmit the measured refractive index and temperature of the sample via communication bus 240, or wirelessly via radio connection, to portable IHS 205. Alternatively, the user may observe the measured refractive index and temperature of the sample on display 250 and, in response, manually input this information into portable IHS 205 by adjusting refractive index dial 711 and temperature dial 713 to the observed readings.

In a scenario where refractometer 235 connects to portable IHS 205 via communication bus 240, refractometer 235 automatically transmits the measured refractive index and temperature information of the liquid sample to portable IHS 205. In response, main mode screen 700 displays refractive index (nD or ns) on the numerical display section 711A of refractive index dial 711. No manual information entry is needed in this case. However, in a manual data entry scenario, the user may observe the refractive index of the sample on refractometer 235 and input the observed refractive index, ns, on dial portion 711B of refractive index dial 711. To perform this input task, the user touches the numbered region of dial portion 711B and moves the dial laterally left or right until the observed refractive index appears below marker 711C. The user may also observe the refractive index value changing in numerical display section 711A until the desired value, for example ns=1.33509, is displayed. Display section 711A provides fine tuning of the refractive index to the observed value. In a similar manner, the user may also input the observed temperature from the refractometer 235 into temperature dial 713.

Inputs 705 also include dose input dial 715 and beverage input dial 717. In one embodiment, dose input dial 717 is the weight in grams (g) of ground coffee in a particular recipe, e.g. 56 g. In this particular example, beverage input dial 717 displays the amount of brew water in volume, e.g. 1.00 L. In another embodiment, beverage input dial 717 shows the amount of brew water in weight. The particular units and values for dose input dial 715 and beverage input dial 717 are selectable, as explained below in more detail. In a manner similar to that of refractive index dial 711, the user may select input values for dose weight dial 715 and beverage input dial 717.

Using the input values selected on dose input dial 715, beverage input dial 717, refractive index input dial 711 and temperature input dial 713, the processor 210 of portable IHS 205 determines the corresponding extraction yield in terms of percent extraction (% EXT) and total dissolved solids (% TDS). In actual practice, liquid design application 105 determines the % extraction yield (% EXT) from the dose, brew water amount and % total dissolved solids (% TDS). Liquid design application 105 determines % total dissolved solids (% TDS) from the refractive index and temperature that the refractometer 235 measures.

Liquid design application 105 employs a surface plot of the correlation of refractive indexes ($n_S$) and corresponding concentrations and temperatures on a single scale. This arrangement allows a single scale to replace a very large number of scales for a particular liquid under test. Liquid design application 105 employs a 3 dimensional scale that relates refractive index ($n_S$), concentration and temperature together on single scale for a particular liquid substance under test. In one embodiment that employs a correlation scale determined using a 3D surface plot, a single advanced polynomial equation may fit and apply to an entire range of refractive indexes, temperatures and concentrations. The polynomial equation describes the surface of, and fits the curve of, the 3D plot of refractive indexes, temperatures and concentrations for the particular substance under test.

Before using refractometer 235 to take refractive index and temperature measurements, the user may select the gear-shaped preferences icon 730 to gain access to user preferences in the current mode, namely coffee mode. In preferences screen 800 of FIG. 8A, the user may select the refractometer type by touching refractometer type box 805. In response to touching refractometer type box 805, liquid design application 105 generates refractometer type selection screen 830 as seen in FIG. 8B. In refractometer type selection screen 830, the user may select a native refractometer mode box 835 or a TDS (% TDS) box 840. If the user selects native refractometer mode box 835, then liquid design application 105 uses index of refraction and temperature information received from refractometer 235. In response, liquid design application 105 will determine the extraction yield and total dissolved solids from the native refractive index and temperature received as input from refractometer 235, as well as the dose weight and brew water volume input information. However, if the refractometer 235 is the type that reads directly in TDS output, then the user may select % TDS box 840. Alternatively, if the user selects % TDS, then liquid design application 105 determines the extraction yield and a total dissolved solids the TDS input information received from refractometer 235 together with the dose weight and brew water volume input information.

Figure 8A:
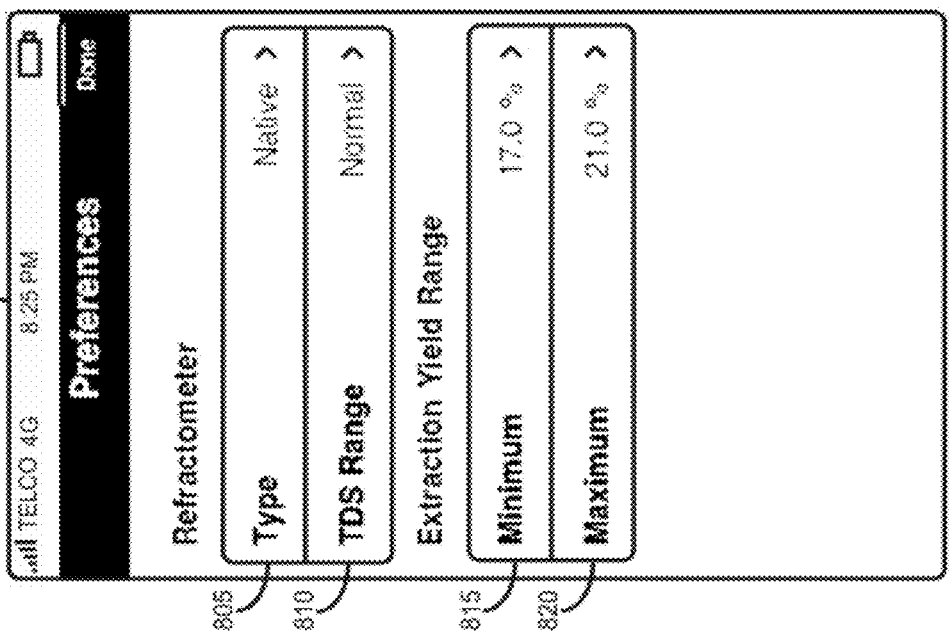
FIG. 8A shows a preferences screen of the disclosed liquid design application.
Figure 8B:
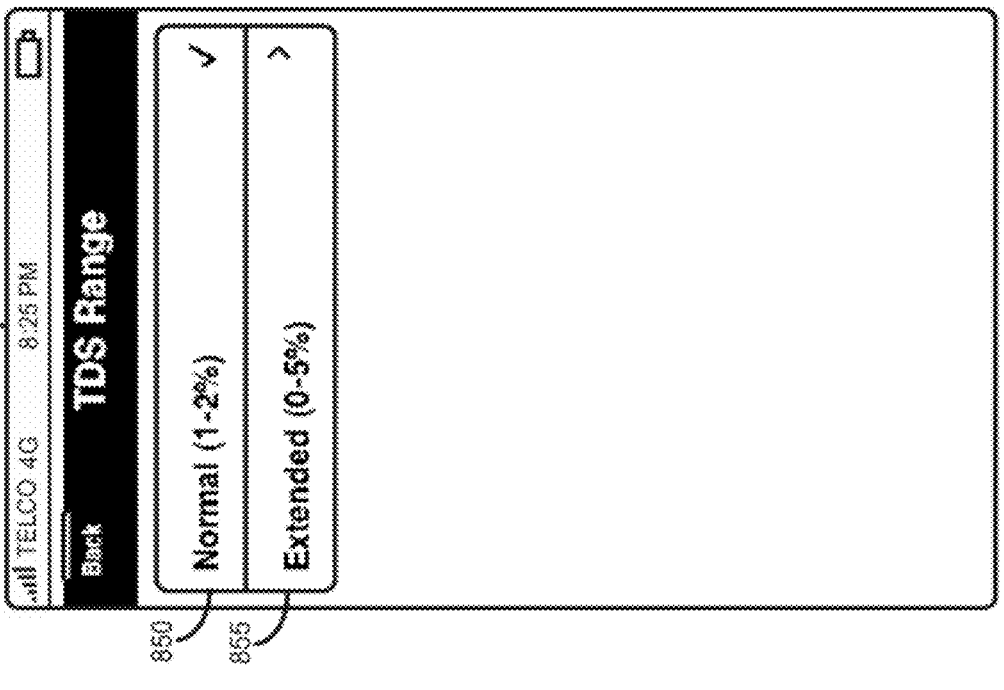
FIG. 8B shows a refractometer type selection screen of the disclosed liquid design application.
Figure 8C:
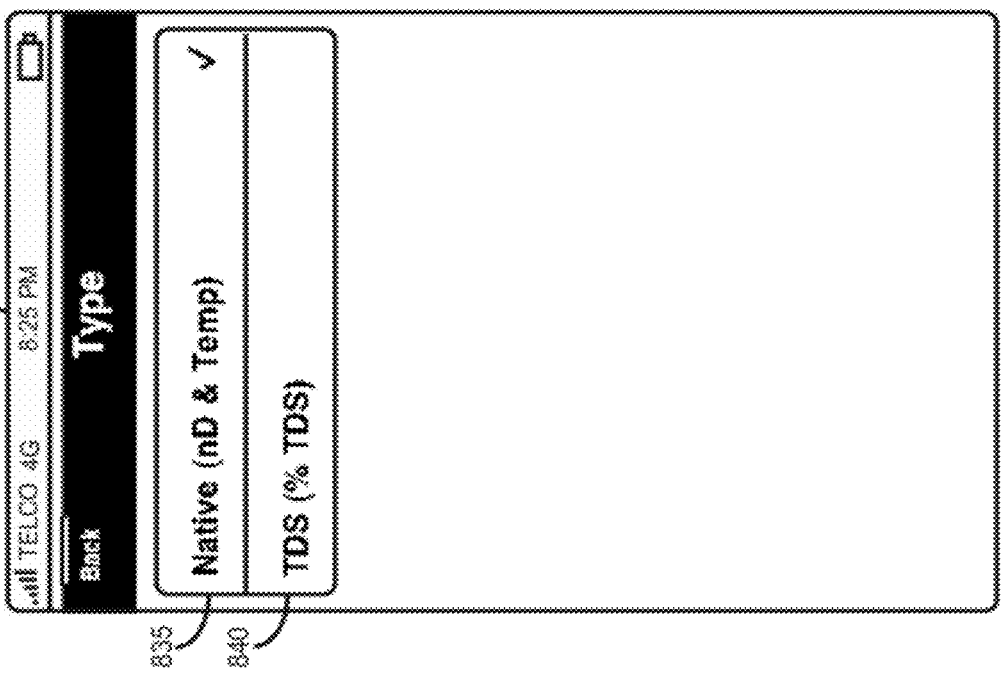
FIG. 8C shows a TDS range screen of the disclosed liquid design application.

Returning to the preferences screen 800 of FIG. 8A, the user may select the TDS range by touching TDS range box 810. When the user selects TDS range box 810, liquid design application 105 responds by generating TDS range screen 845 of FIG. 8C. On TDS range screen 845, the user may select normal box 850 to provide a TDS range of desired concentration which is "normal", for example with a 1-2% variation. Alternatively, the user may select an "extended" range, for example box 855 which results in a 0-5% variation. Variations outside of these ranges may be used in other embodiments depending upon the particular liquid under test. In this particular example, the user selects a normal TDS range by selecting normal box 850. In response to selecting normal range box 850, liquid design application 105 generates a minimum value range screen 860 as shown in FIG. 8D. In this example, the user touches the box corresponding to 17% to set the minimum value of the TDS range to 17%. To set the maximum value of the TDS range, the user selects the box corresponding to 21%, for example, as shown in the maximum value range screen 865 of FIG. 8E.

Figure 9A:
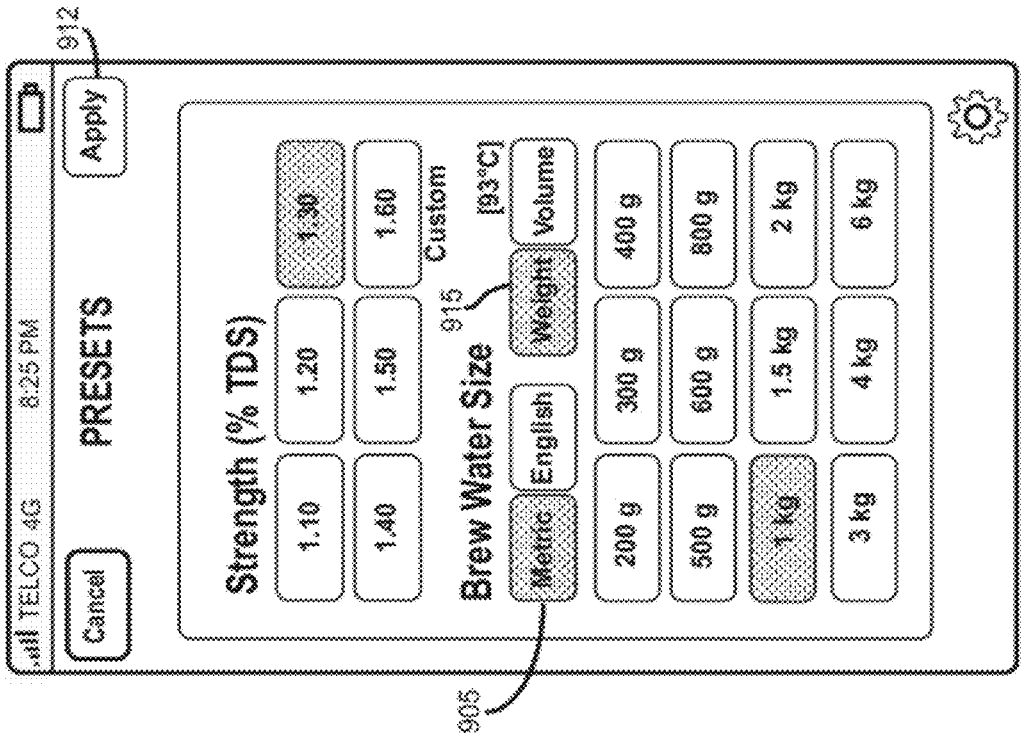
FIG. 9A shows a presets screen with metric volume units being selected.

Returning to the main coffee mode screen 700 of FIG. 7, the user may select drawer icon 735 to access a presets screen 900 as shown in FIG. 9A. Presets screen 900 includes several different preset strengths (% TDS) that the user may select by touching boxes labelled 1.10, 1.20, 1.30, 1.40, 1.50 and 1.60% TDS. For example, 1.3% TDS is a generally acceptable coffee strength that falls within internationally accepted standards for proper brewing protocols. To select a 1.3% TDS preset strength value, the user selects the 1.3% TDS box that becomes highlighted in response. The 1.60% TDS box is customizable should the user chose to do so by selecting the 1.60% TDS box and setting that box to any desired custom TDS value.

The user may also set the liquid size, i.e. the brew water size, to a number of preset values that are available in a number of different metric or English system units. For example, the user may desire to brew coffee using metric units of volume at a predetermined temperature of 93 degrees C. To do so, the user selects the metric box 905 and volume box 910. To signify that the user selected metric box 905 and volume box 910, these boxes are highlighted upon selection. In response to selection of metric box 905 and volume box 910, liquid design application 105 generates a 4×3 matrix of preset metric volume boxes, each box being labelled with a respective metric volume that the user may select depending on the desired brew water size. In this particular example, the user may select from metric volume boxes labelled 200 ml, 300 ml, 400 ml, 500 ml, 600 ml, 800 ml, 1 L, 1.5 L, 2 L, 2.5 L, 3 L, 4 L and 6 L. In the example of FIG. 9A, the user selected the 1.3% TDS box for coffee strength and the 1 L box for brew water size, as indicated by highlighting. To apply these volume presets to main mode screen 900 of FIG. 9A, the user selects "apply" box 912. One applied, these presets may be further refined by use of the adjustment 717, to any desired value, for example 365 ml.

Figure 9B:
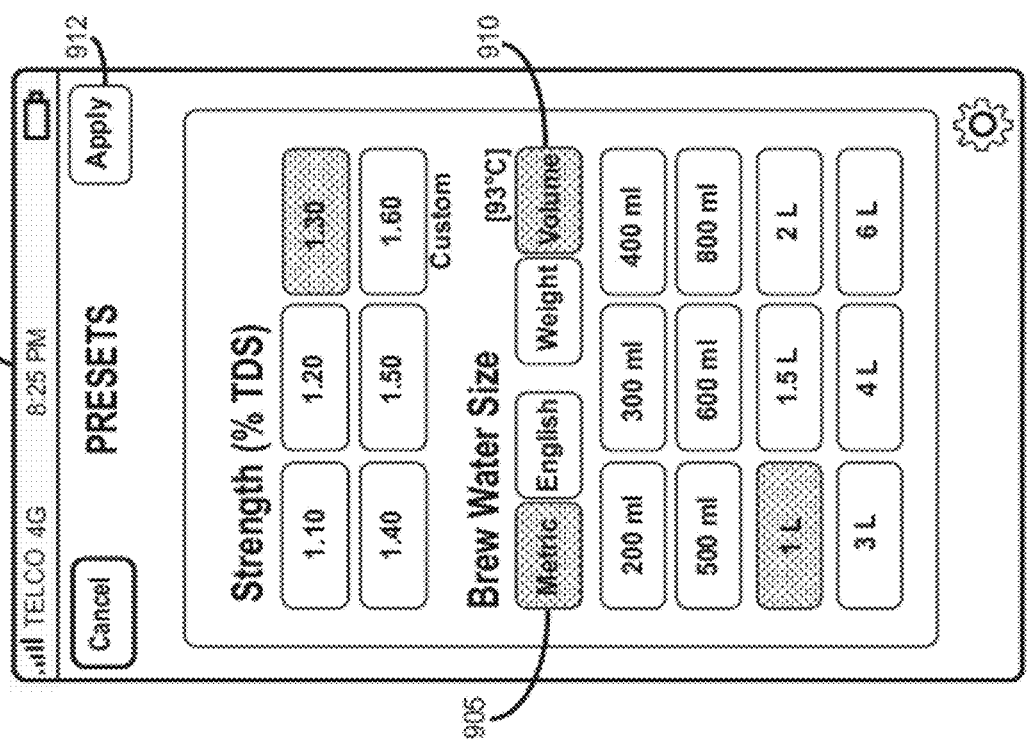
FIG. 9B shows a presets screen with metric weight units being selected.

Liquid design application is capable of changing between metric volume, metric weight, English volume and English weight presets on the fly, i.e. in real time. For example, while the user first selected metric volume units for brew water size in the example of FIG. 9A, the user may instead desire metric weight units for the brew water size preset. To switch the 4×3 matrix of preset metric volume boxes to metric weight, the user selects metric box 905 and weight box 915 as shown by highlighting of these boxes in FIG. 9B. In response to such selection, coffee design application 105 regenerates the 4×3 matrix of brew water size presets in metric weight units. In this particular example, the user may now select from metric weight boxes labelled 200 g, 300 g, 400 g, 500 g, 600 g, 800 g, 1 kg, 1.5 kg, 2 kg, 2.5 kg, 3 kg, 4 kg and 6 kg. In the example of FIG. 9B, the user selected the 1.3% TDS box for coffee strength and the 1 kg box for brew water size, as indicated by highlighting.

Figure 9C:
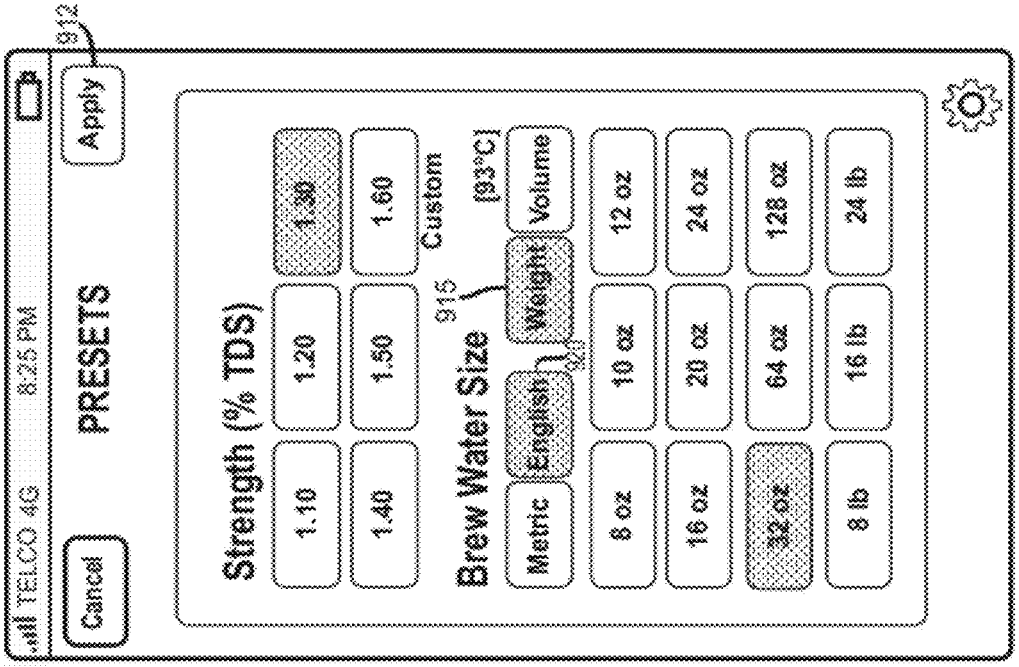
FIG. 9C shows a presets screen with English volume units being selected.

To switch to English volume units, the user touches English box 920 and volume box 910 as indicating by highlighting in FIG. 9C. In response to such selection, coffee design application 105 regenerates the 4×3 matrix of brew water size presets in English volume units. In this particular example, the user may now select from English volume boxes labelled 8 fl oz, 10 fl oz, 12 fl oz, 16 fl oz, 20 fl oz, 24 fl oz, 32 fl oz, 64 fl oz, 1 Gal, 1.5 Gal, 2 Gal and 3 Gal. In the example of FIG. 9C, the user selected the 1.3% TDS box for coffee strength and the 32 fl oz box for brew water size in English volume units, as indicated by highlighting of these respective boxes.

Figure 9D:
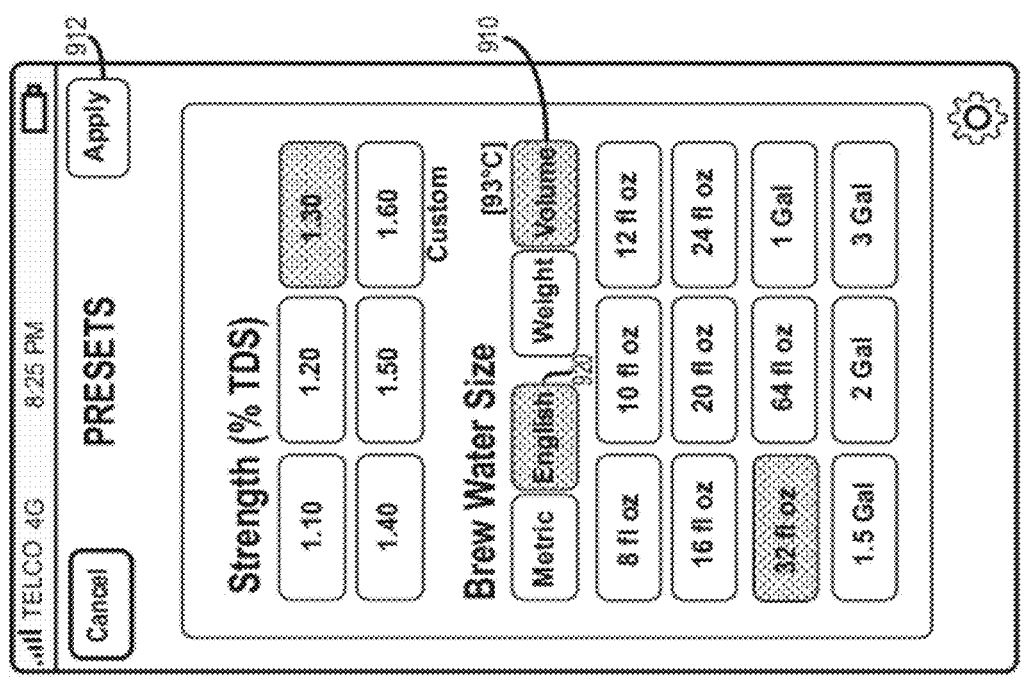
FIG. 9D shows a presets screen with English weight units being selected.

To switch to English weight units, the user touches English box 920 and weight box 915 as indicating by highlighting in FIG. 9D. In response to such selection, coffee design application 105 regenerates the 4×3 matrix of brew water size presets in English weight units. In this particular example, the user may now select from English weight boxes labelled 8 oz, 10 oz, 12 oz, 16 oz, 20 oz, 24 oz, 32 oz, 64 oz, 128 oz, 8 lb, 16 lb and 24 lb. In the example of FIG. 9D, the user selected the 1.3% TDS box for coffee strength and the 32 oz box for brew water size in English weight units, as indicated by highlighting of these respective boxes.

Figure 9E:
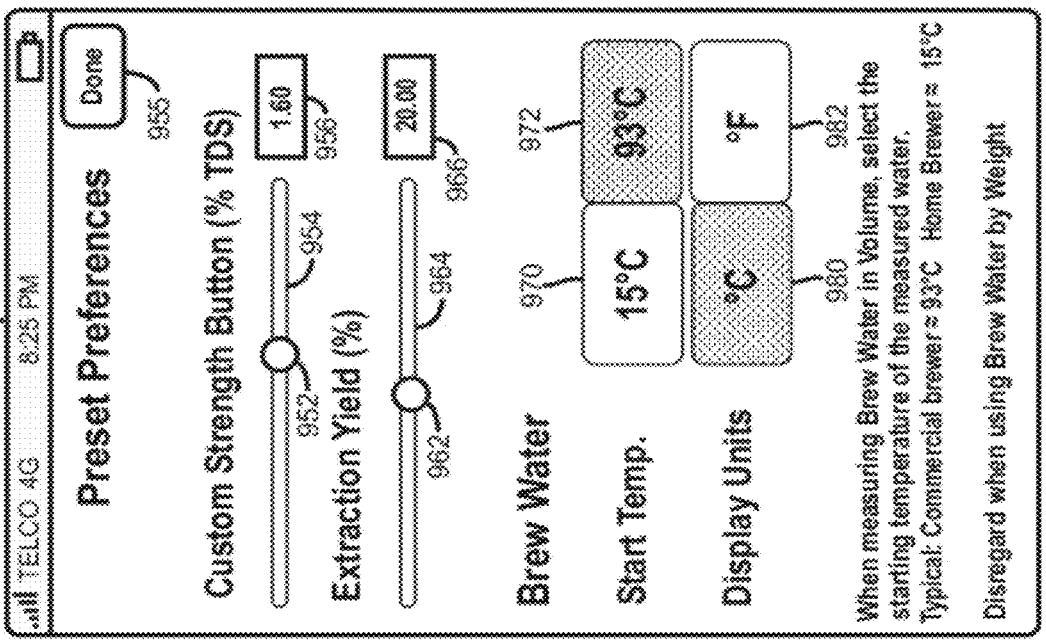
FIG. 9E shows a preset preferences screen.
Figure 10E:
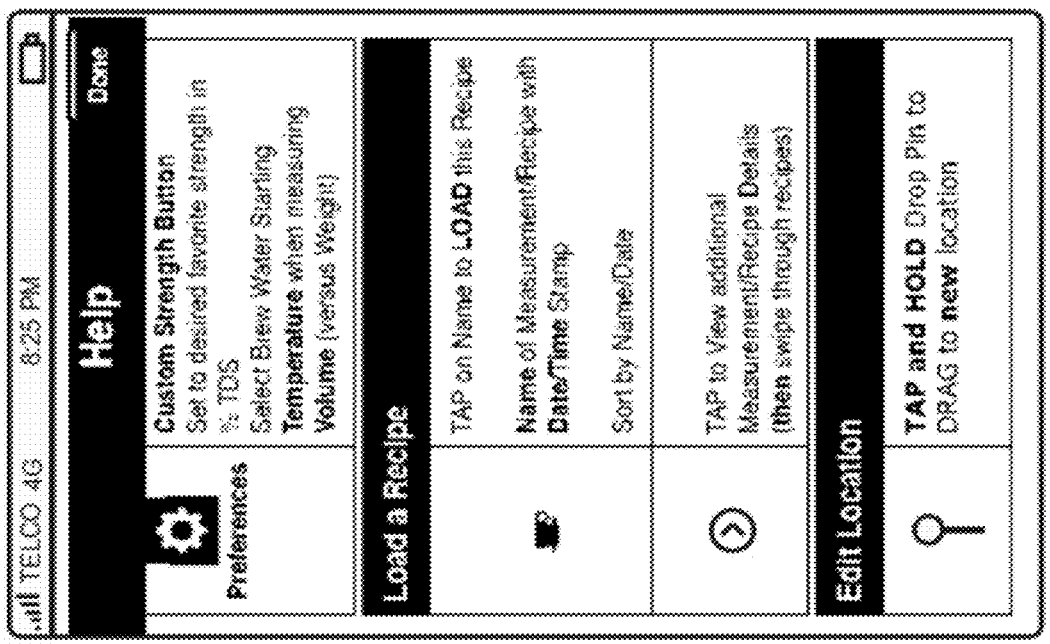

FIG. 9E shows a preset preferences screen 950 that the user may access by selecting folder icon 740 of main coffee mode screen 700 of FIG. 7. Upon accessing preset preferences screen 950, the user may select a custom brew strength (% TDS) by moving button 952 on slider bar 954 laterally left or right until the desired % TDS value appears in box 956. In this particular example, the user selects a custom % TDS value of 1.6% for the brew strength. The user may also set the extraction yield (%) by moving button 962 on slider bar 964 laterally left or right until the desired % extraction yield value appears in box 966. In this particular example, the user selects a % extraction yield value of 20.00%.

The user may also set the brew water starting temperature by touching starting temperature box 970 to select 15° C. as the starting temperature for brewing. Alternatively, the user may select starting temperature box 972 to select a starting temperature of 93° C. In the example of FIG. 7E, the user touched starting temperature box 972 as indicated by highlighting or shading of that box. In response to this selection, liquid design application 105 employs 93° C. as the starting temperature for coffee brewing parameter determination. To select units in Celsius (° C.), the user touches display ° C. units box 980. To select units in Fahrenheit (° F.), the user touches display ° F. units box 982. When the user is done with preset preferences screen 950, the user selects done box 985. In response, liquid design application 105 employs the selections made by the user on preset preferences screen 950.

Returning now to FIG. 7 and assuming that the user selected a preset recipe of 1.3% TDS for brew strength and 1 L as the brew water size on preset screen 900 of FIG. 9, these presets apply to the main coffee mode screen 700. More particularly, as seen in FIG. 7, brew water volume input dial 717 exhibits a 1 L value and total dissolved solids (% TDS) output dial exhibits a 1.28% value which is approximately 1.3%. The user may adjust the precise TDS % exhibited by TDS % dial 723 that is desired by touching the dial numbers (e.g. number 1.5) adjacent indicator line 740 and moving these numbers left or right laterally to the desired value. In this particular example, the liquid sample under test exhibits a measured refractive index of 1.33509 and a measured temperature of 22° C., as seen on refractive index dial 711 and temperature dial 713, respectively. From the input information on refractive index dial 711, temperature dial 713, dose dial 715 and brew water dial 717, liquid design application processes an advanced polynomial equation, as discussed in more detail below, to provide output results, namely the resultant extraction yield and the total dissolved solids (% TDS). The resultant extraction yield and % TDS are displayed on outputs 720. More specifically, extraction yield (% EXT) dial 721 displays the extraction yield output value and % TDS dial 723 displays the total dissolved solids output value.

For help in operating liquid design application 105 in coffee mode, the user may select coffee mode help button 535 in main mode screen 700 of FIG. 7. In response to the user's selection of coffee mode help button 535, liquid design application 105 generates the scrollable help screen that FIGS. 10A-10E depict. While FIGS. 10A-10E depict multiple overlapping screens, these screens actually form one continuous help screen through which the user may scroll with his or her finger in one embodiment. The coffee mode help screen that FIG. 10A-10E together depict explains to the user at a high level the operation of liquid design application while defining several terms and features.

Figure 11B:
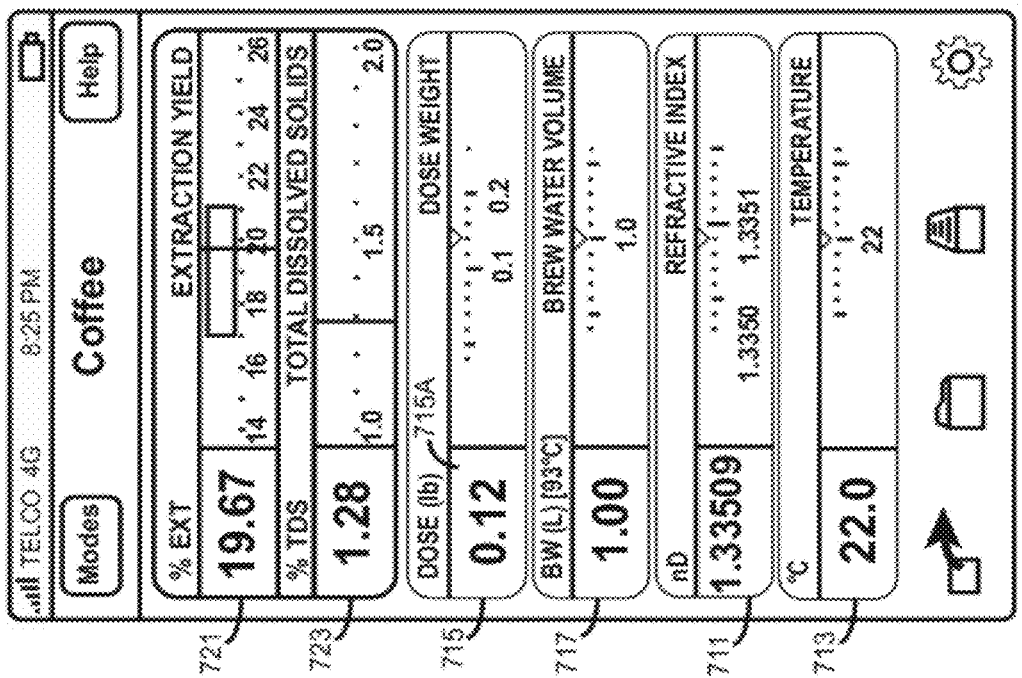
FIG. 11A-11E show the units selection capability of the disclosed liquid design application.
Figure 11A:
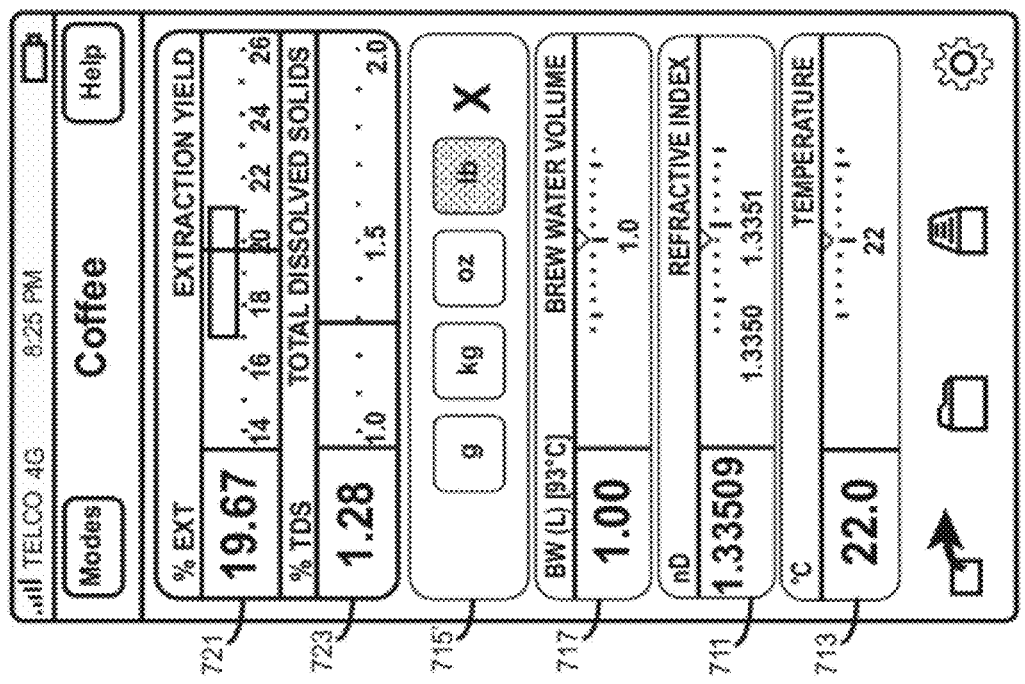
Figure 11C:
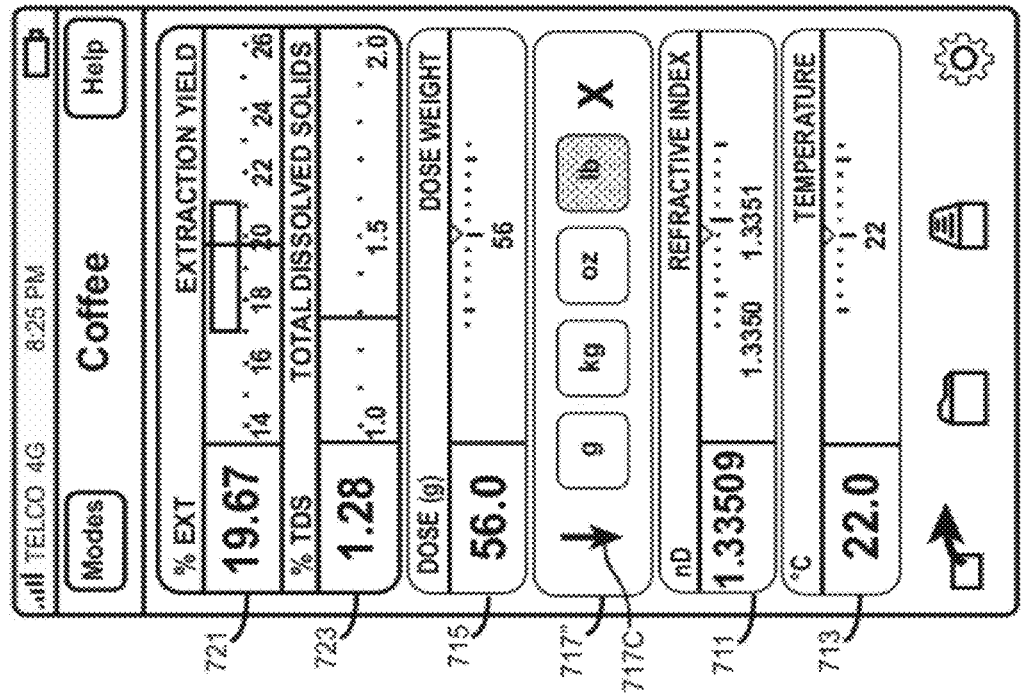

Referring now to both FIG. 7 and FIG. 11A, the user may instruct liquid design application 105 to change the units of measure for the dose by double tapping dose numeric display section 715A of FIG. 7. FIG. 7 shows the dose set currently to 56.0 grams. Liquid design application 105 may also express that value in terms of kilograms (kg), ounces (oz) or pounds (lb). To make this selection of alternative units for the dose, the user selects a units change mode by double tapping dose numeric display section 715A. In response to this selection, liquid design application 105 displays the main coffee mode screen of FIG. 11A wherein the dose dial 715 changes to units selector 715'. Units selector includes a grams button (g), a kilograms button (kg), an ounces button (oz) and a pounds button (lb). In this example, the user desires to have the coffee display in weight by pounds, so the user selects the pounds button (lb) as indicated by the highlighted pounds button (lb) in FIG. 11A. In response to this selection, liquid design application 105 converts the 56 gram dose to a 0.12 lb dose as indicated in display section 715A of FIG. 11B.

Figure 11D:
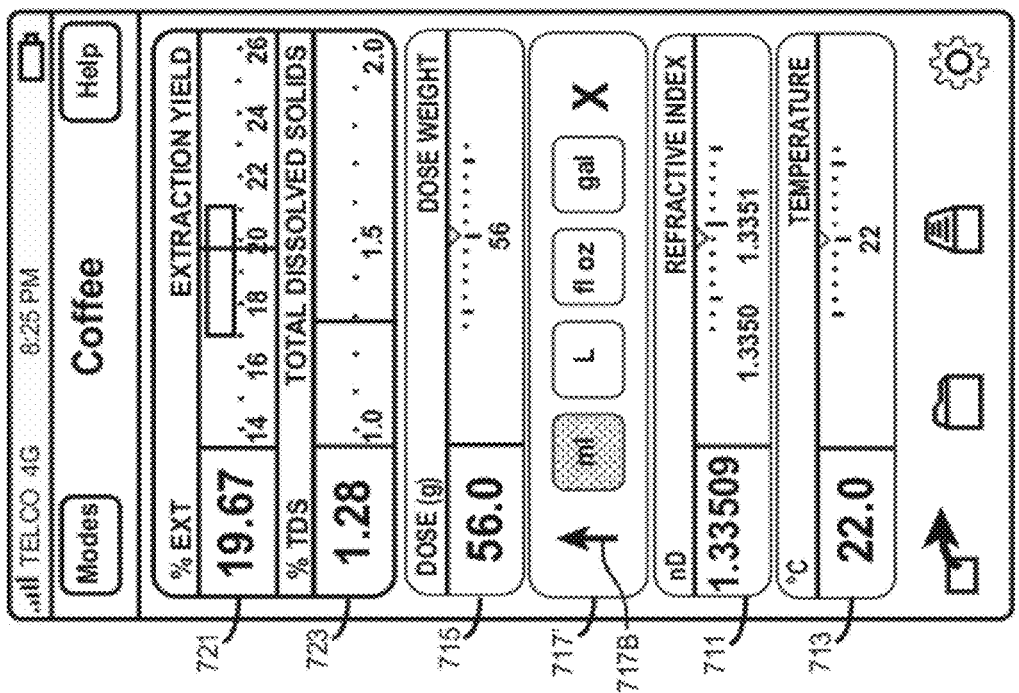
Figure 11E:
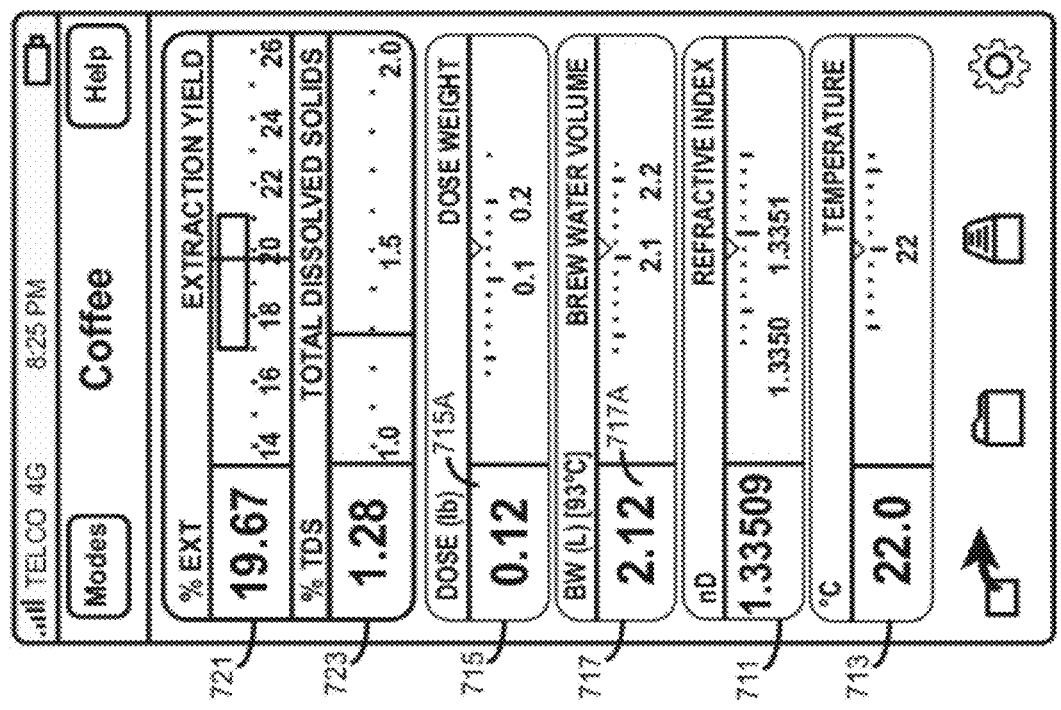

Liquid design application 105 may also convert the quantity of brew water to metric/English volume units or metric/English weight units. To initiate this units conversion, the user double taps brew water (BW) display section 717A of FIG. 7. In response, liquid design application 105 displays the main coffee mode screen of FIG. 11C wherein brew water (BW) dial 717 changes to metric/English volume units selector 717'. Metric/English volume units selector 717' includes a milliliter button (ml), a liter button (L), a fluid ounce button (oz) and a gallon button (gal) and an up arrow 717B. For example, the user may select milliliter button (ml) on units selector 717 of FIG. 11C and, in response, the brew water (BW) dial 717 will display in milliliter units (ml) instead of liter units (L) as it did previously. Note: This conversion of water volume to mass takes into account water density as a function of measurement temperature, so that the brew formula is adjusted and corrected accordingly. For example, 1-Liter of water measured at 94 degrees C. weighs 963 grams, whereas if the brew water is measured at 15 degrees C., before heating to be brewed, it weighs 999 grams. Accordingly, the application corrects the coffee dose required as a function of water temperature. However, liquid design application 105 may also convert the former one liter (L) of brew water displayed on brew water (BW) dial 717 to pounds (lb) by tapping up arrow 717B. When the user selects up arrow 717B by tapping, liquid design application 105 displays a metric/English mass/weight units selector 717" that includes a gram button (g), a kilogram button (kg), an ounces button (oz) and a pounds button (lb) as seen in FIG. 11D. Up arrow 717B is replaced by down arrow 717C in FIG. 11D. Down arrow 717C signifies that the user may change from mass/weight units to volume units by tapping on down arrow 717C. In this example, the user selects pound button (lb) as signified by highlighting of that button in FIG. 11D. In response to this selection, liquid design application 105 converts the form 1 L metric volume to 0.12 pounds (lb) as seen in display section 717A of FIG. 11E.

Referring again to FIG. 7, the user may employ liquid design application 105 to change the recipe for the brewed coffee and observe the impact of changing the recipe on the extraction yield (% EXT) of the resultant brewed coffee. Assume that the user selects presets in preset screen 900 of FIG. 9A that set the coffee recipe to the recipe depicted in main coffee mode screen 700 of FIG. 7. In other words, the user sets the coffee recipe to a dose of 56 g of coffee, a brew water (BW) volume of 1 L, and a % TDS of 1.28 as seen in FIG. 7.

Extraction yield dial 721 includes a range box 721A that displays a range or region of interest 721A including a minimum % EXT value 721B of 17% and an maximum % EXT value 721C of 21%, in this particular example. Maximum value 721C and minimum value 721B may also be referred to as limits, outside of which the final beverage quality result will be unacceptable. If after the user brews, and measures actual Ext % results, the % EXT value falls outside of these limits, then liquid design application 105 provides a visual cue as an "outside of preferred range" indicator. One way in which liquid design application 105 provides an outside of preferred range indicator is to change the background color of % EXT display section 721D, as explained in more detail below, or an audio alert can be sounded. The current value of % EXT is 19.67 which is within the range limits of 17 (721B) and 21% 721C EXT (Extraction Yield). Since the current value of % EXT is within the prescribed acceptable range of interest, the color of % EXT display section 721D does not change. However, if the user's measurements indicate that the % EXT falls outside of the prescribed range, then liquid design application 105 changes the color of % EXT display section 721D to alert the user, as explained in more detail below.

To optimize or otherwise change the recipe of the coffee, the user may wish to change the brewing technique in order to achieve more or less concentration, and thus extraction yield. This results in a measurement of refractive index that changes, and thus the % TDS will follow up or down, changing the Extraction Yield in the desired direction until it is within prescribed limits of 17-21%.

Figures 12A, 12B:
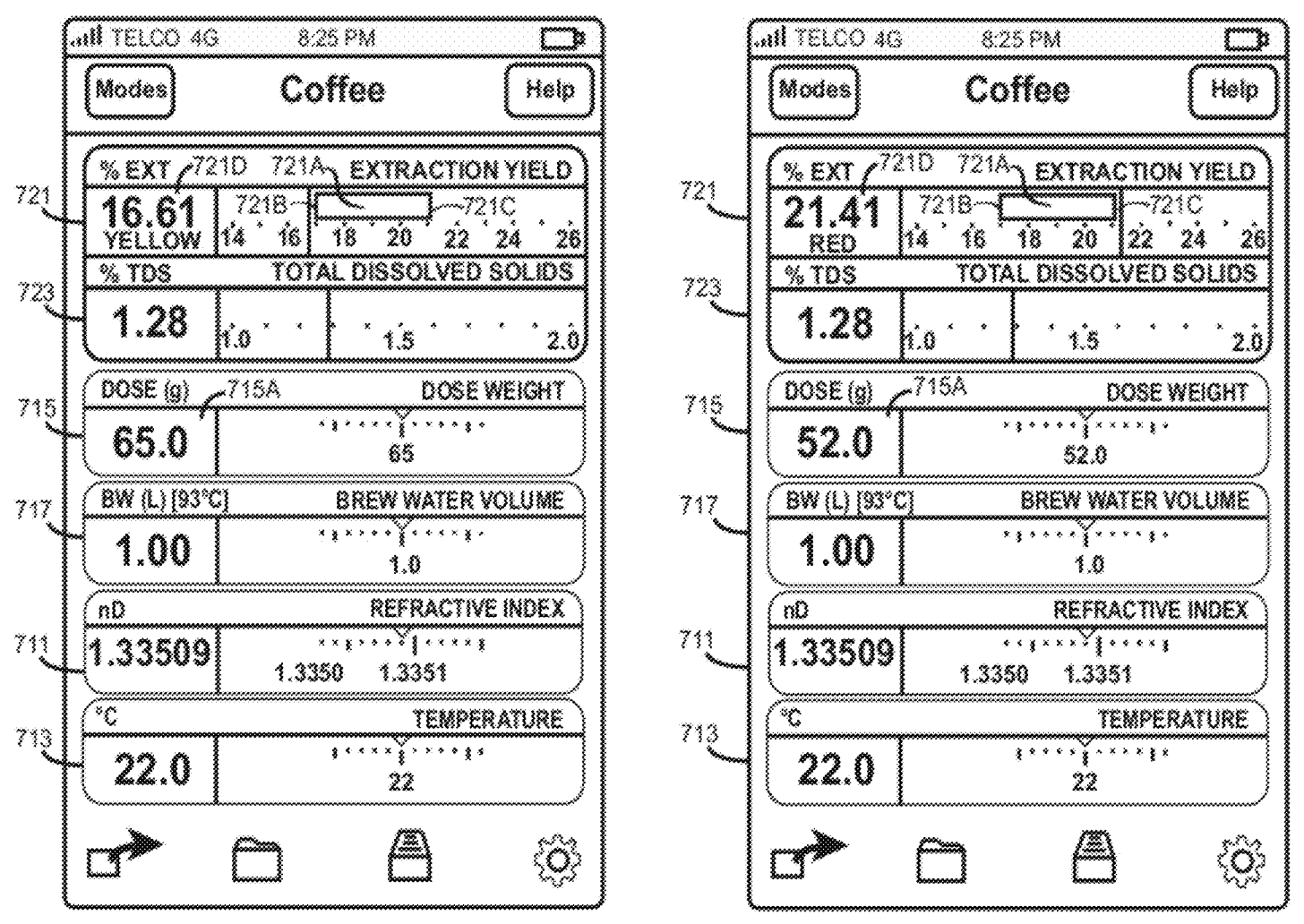

Using the above-described technique, the user may change brewing factors, such as grade of grind and or length of brew time and increase the concentration from a previous value of 1.40% TDS to a new value of 1.40% as indicated by a measurement of 1.3353 nD at 22.0 degrees C., thus increasing Ext to 21.52 which may be bitter. In response, liquid design application 105 displays a value of 21.52 in % EXT display section 721D with a RED background as shown in FIG. 12B. The RED background alerts the user that the current recipe is outside of the preferred range of 17% to 21% on the high side, which is known to generate bitter taste defects in the final beverage. The user may take corrective action by altering the brewing protocols such that the % EXT is within the preferred range.

Alternatively, the user may change and decrease the dose from a preset value of 56 g to a new recipe value of 52 g by using dose dial 715 in order to reduce strength, but still try to achieve a desired extraction yield within acceptable limits of 17-21%. Changing the dose to a new recipe value of 52 g and targeting an EXT extraction yield of 20% results in a strength reduction to 1.18%. In response, liquid design application 105 displays a value of nD of 1.3349 at 22.0 Deg C., which is the new targeted value for a less concentrated brew strength.

Figure 12C:
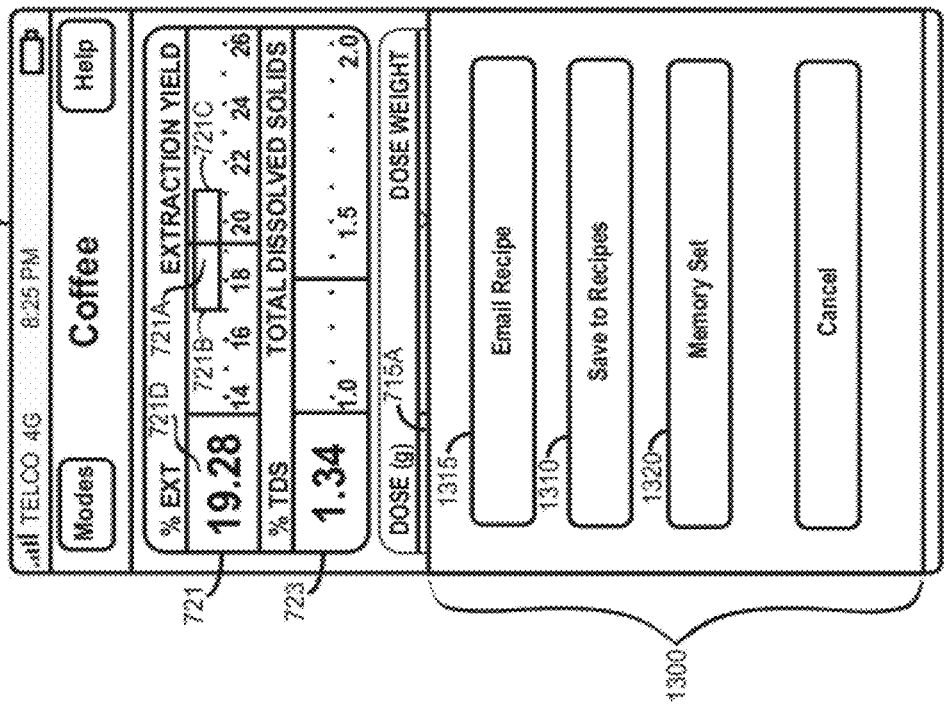
FIG. 12C shows the main screen of the liquid design application indicating that the extraction yield is inside of the range of interest between the upper and lower trigger points.

When the user sees that the final measurement of any recipe results in a % EXT that is outside of the prescribed range, the user may adjust the brewing protocol to take corrective action and bring the % EXT back within the prescribed range. For example, the user may change brewing protocols by adjusting grade of grind up or down to obtain the value of concentration as shown on dose dial 723 of FIG. 12C. In response, liquid design application 105 determines the corresponding extraction yield (% EXT) to be 19.28 and displays the value 19.28 in % EXT display section 712D as shown in FIG. 12C. This value is within the prescribed % EXT range.

After the user adjusts dosage and finds a coffee recipe that is desirable for future use, liquid design application 105 may save that recipe and measurement for the user. Alternatively, the recipe may be shared with other users via email or other type of transmission, as discussed further below. With respect to saving the recipe, assume that the user finds the coffee recipe depicted in FIG. 12C to be desirable. This particular recipe specifies a dose of 59.5 g coffee, a brew water volume of 1 L, a brew temperature of 22° C., a total dissolved solids (% TDS) value of 1.34% and an extraction yield of (% EXT) of 19.28%. This recipe was designed by the user when liquid design application 105 read an index of refraction (refractive index) value for the brewed coffee of 1.33520. To save this recipe, the user selects action button 745 on the main coffee mode display of FIG. 12C. In response to this selection, liquid design application 105 superimposes a selection window 1300 over main coffee mode screen 1305 of FIG. 13A. Selection window 1300 includes a save to recipes button 1310 that the user may select to instruct liquid design application 105 to save the current recipe to non volatile memory 220 of FIG. 2. Save to recipes button 1310 may cause the recipe to be saved by saving the recipe in an integrated database, to save via posting to a public web site, to save via the Internet to any from of on-line database.

Figure 13A:
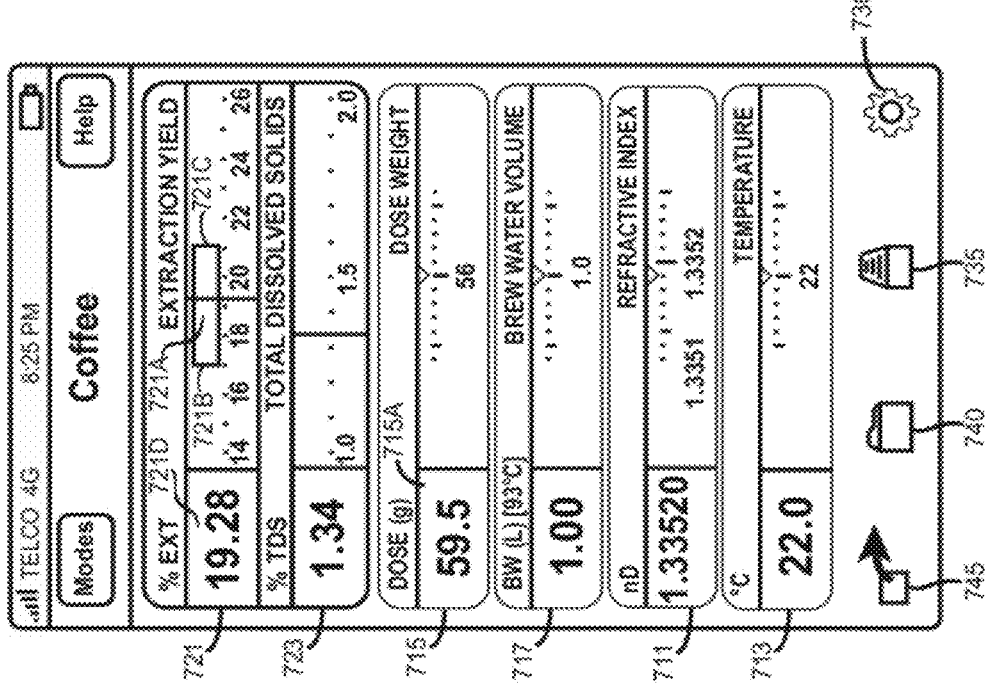
FIG. 13A-13F illustrate representative screens showing one method wherein the liquid design application saves recipe information.
Figure 13C:
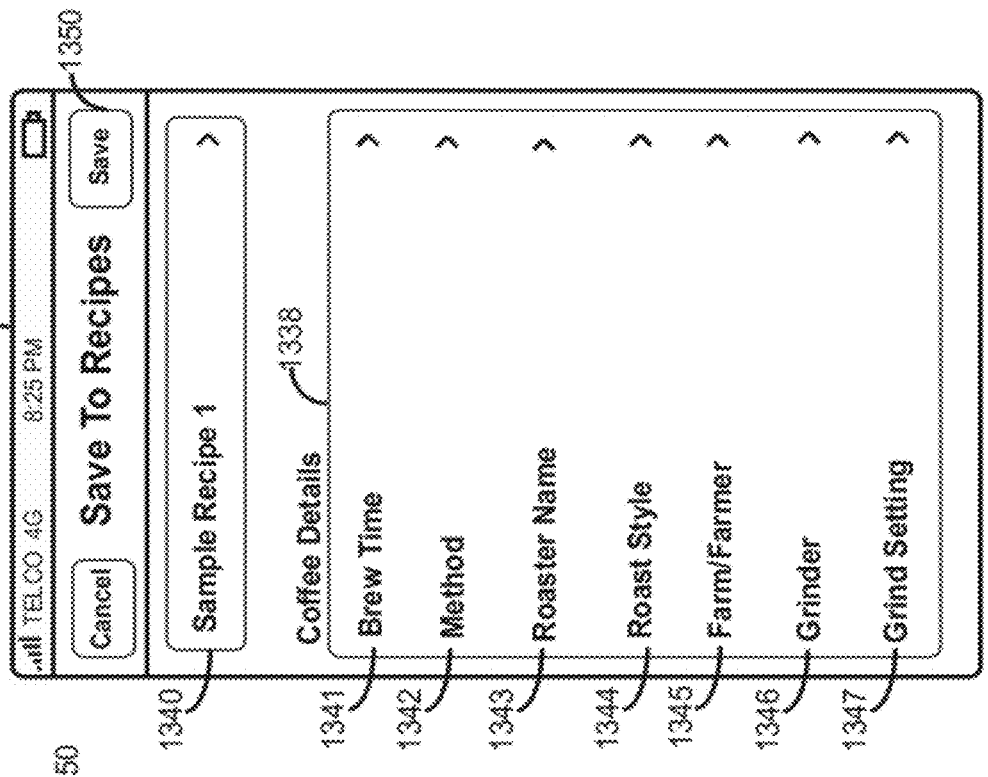
Figure 13B:
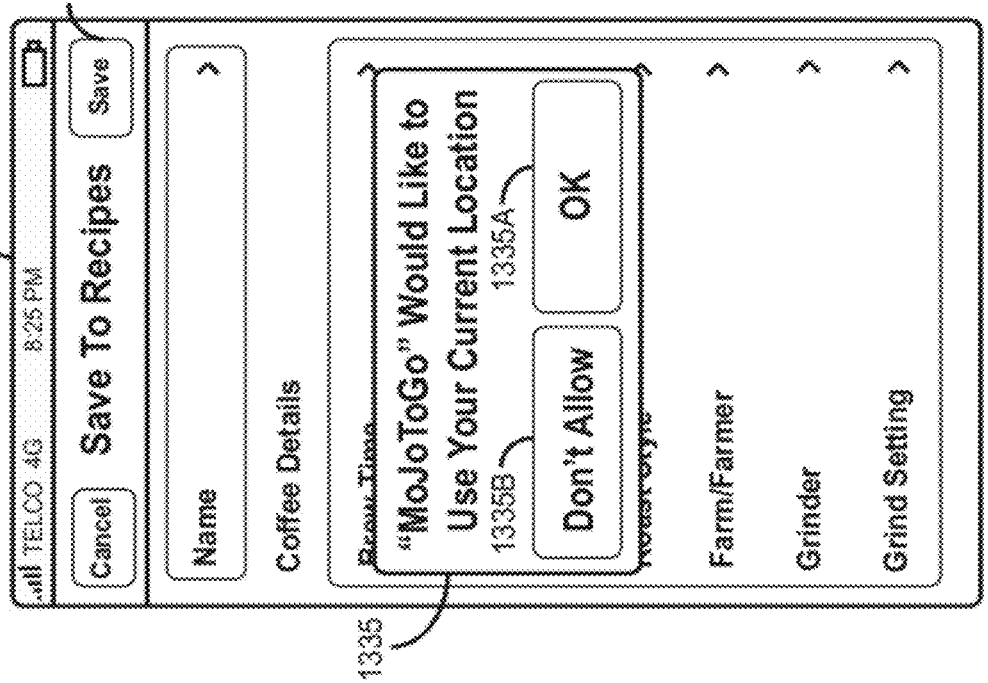

In response to selecting the "save to recipes" button 1310, liquid design application 105 generates the "save to recipes" screen 1330 shown in FIG. 13B. Liquid design application 105 initially superimposes a location dialog box 1335 as seen in FIG. 13B. Location dialog box 1335 gives the user the option to store the user's current geographic information, as determined by GPS 285, in non-volatile memory 202 as part of the recipe information therein. The user selects OK button 1335A to allow such storage, or alternatively selects "Don't Allow" button 1335B to not allow storage of the current location.

After selection of either OK button 1335A or "Don't Allow" button 1335B, liquid design application 105 removes location dialog box 1335 from "save to recipes" screen 1330, leaving "save to recipes" screen 1330 FIG. 13B on the display as seen in FIG. 13C. The user may select "recipe name" box 1340 to input a name for the recipe, for example "Sample Recipe 1" as shown in FIG. 13C. The user may type or otherwise input the recipe name and other recipe information into liquid design application 105. For example, the user may select "recipe name" box 1340 by touching the arrow 1340A in the rightmost portion of recipe name box 1340. An input box (not shown) then opens up on "save to recipes" screen 1305 to allow the user to type or otherwise input the recipe name information. The user may enter other "Coffee Details" information that describes "Sample Recipe 1" in a similar manner by touching the arrows in the rightmost portion of the following recipe parameters shown in Coffee Details box 1338, namely Brew Time 1341, Method 1342, Roaster Name 1343, Roast Style 1344, Farm/Farmer 1345, Grinder 1346 and Grinding Setting 1347, as well as other recipe information not shown. The user touches Save button 1350 to instruct liquid design application 105 to save the recipe that the user just typed into Save To Recipes screen 1305.

The user may also select email recipe button 1315 of selection window 1300 of FIG. 13A to instruct liquid design application 105 to email the current recipe to a particular programmable email address. Liquid design application 105 may also allow the user to share the recipe via social networking on the Internet. The user may further select memory set button 1320. Memory set button 1320 allows you to display the prescribed design targets so that when you perform the measurement, the user can see how the actual measurement compares with the design target. Liquid design application 105 can save all of the above information for future reference or adjustment.

Figure 13D:
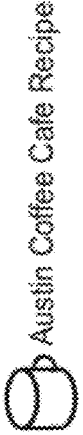
Figure 13E:
Figure 13F:
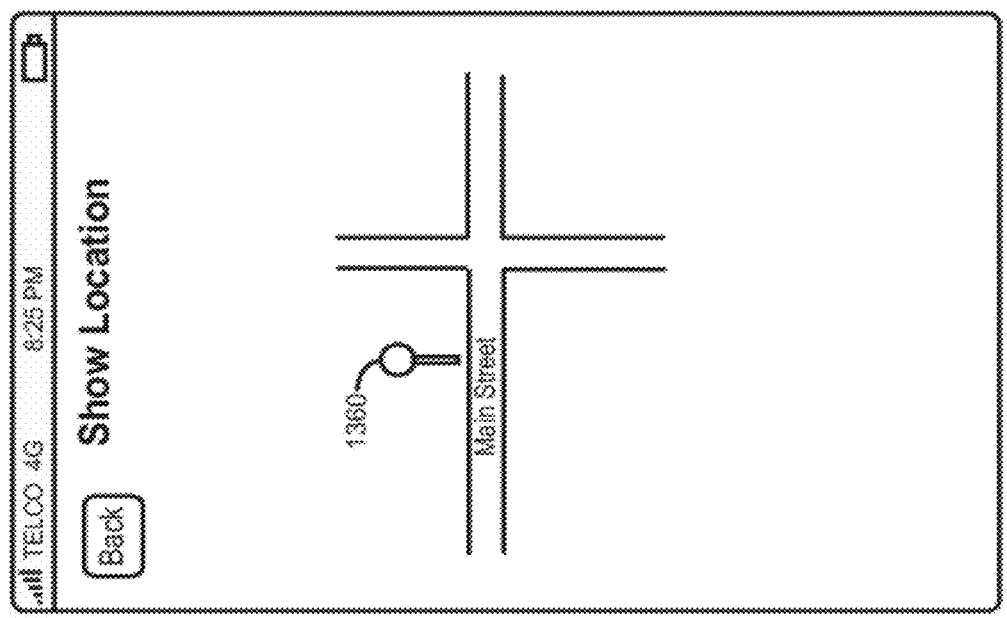

FIGS. 13D and 3E together show details of a particular coffee brew recipe that the user stores in liquid design application 105 for later use. If the user selects map button 1350 of FIG. 13 D or 13E, then liquid design application 105 generates the "Show Location" window of FIG. 13F. In more detail, liquid design application 105 generates a map as shown in FIG. 13F that depicts the current location where the subject coffee is being brewed according to a particular current recipe. The map of FIG. 13F includes a "push pin" 1360 that indicates the geographic location of the coffee recipe that is currently being brewed as derived from the GPS 285 in portable IHS 205.

Figure 14:
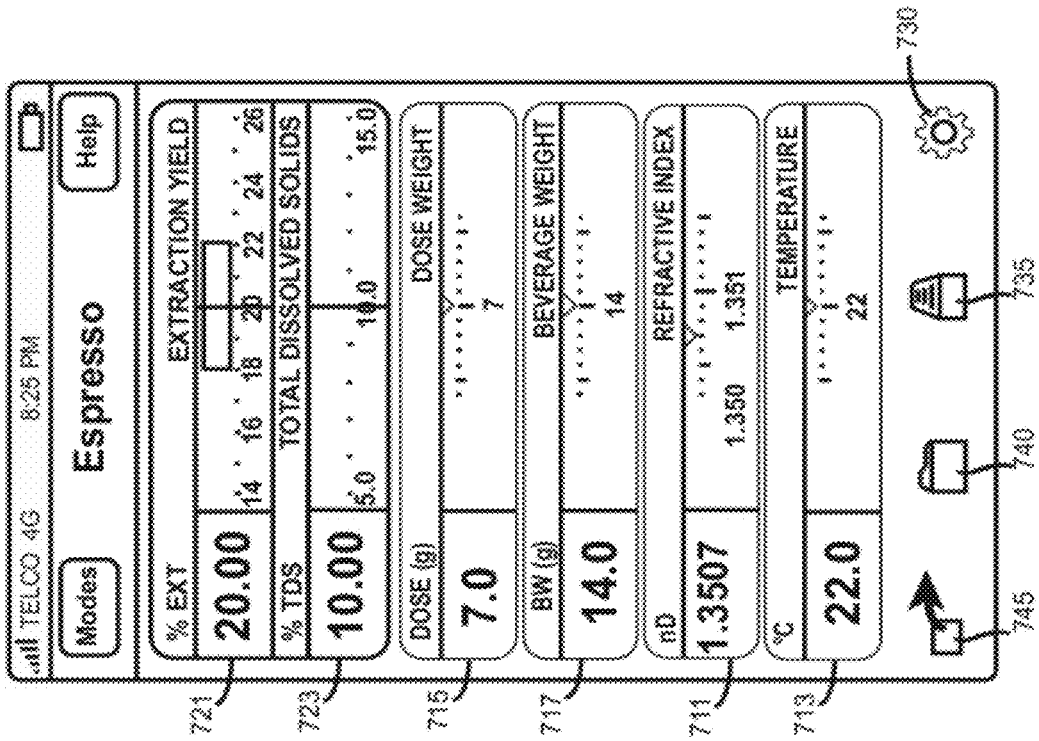
FIG. 14 shows a mode screen for another liquid under test, namely espresso.

FIG. 14 depicts an Espresso mode screen 1400 to illustrate the capability of liquid design application 105 to accommodate multiple modes, for example the Espresso mode of FIG. 14 or other modes such as a sugar mode, a soft drink mode, a human blood mode, a urine mode and other types of liquids. The user may take a refractive index reading for an Espresso sample and then alter the dose to observe the impact on extraction yield (% EXT) until an acceptable Espresso liquid is obtained. The user may save the recipe thus created for later use in a manner similar to saving the recipe as discussed above with reference to FIG. 13A-14F.

TABLE 1 below is a 3 dimensional or 3 variable correlation chart that depicts raw data relating concentration (% TDS) of coffee and refractive index (nD or $n_s$) taken over a wide range of temperatures, for example 15° C.-40° C. in this particular case.

TABLE 1

| % TDS | nD at 15° C. | nD at 20° C. | nD at 25° C. | nD at 30° C. | nD at 35° C. | nD at 40° C. |
|---|---|---|---|---|---|---|
| 0.00 | 1.33340 | 1.33298 | 1.33249 | 1.33193 | 1.33129 | 1.33058 |
| 0.01 | 1.33342 | 1.33300 | 1.33251 | 1.33195 | 1.33131 | 1.33060 |
| 0.02 | 1.33344 | 1.33302 | 1.33253 | 1.33197 | 1.33133 | 1.33062 |
| 0.03 | 1.33346 | 1.33304 | 1.33255 | 1.33199 | 1.33135 | 1.33064 |
| 0.04 | 1.33348 | 1.33306 | 1.33257 | 1.33200 | 1.33137 | 1.33066 |
| 0.05 | 1.33350 | 1.33308 | 1.33259 | 1.33202 | 1.33138 | 1.33067 |
| 0.06 | 1.33351 | 1.33309 | 1.33260 | 1.33204 | 1.33140 | 1.33069 |
| 0.07 | 1.33353 | 1.33311 | 1.33262 | 1.33206 | 1.33142 | 1.33071 |
| 0.08 | 1.33355 | 1.33313 | 1.33264 | 1.33207 | 1.33144 | 1.33073 |
| 0.09 | 1.33357 | 1.33315 | 1.33266 | 1.33209 | 1.33145 | 1.33074 |
| 0.10 | 1.33359 | 1.33317 | 1.33268 | 1.33211 | 1.33147 | 1.33076 |
| . | . | . | . | . | . | . |
| . | . | . | . | . | . | . |
| . | . | . | . | . | . | . |
| 24.00 | 1.376612 | 1.37605 | 1.37526 | 1.37443 | 1.37347 | 1.37262 |

Figure 15:
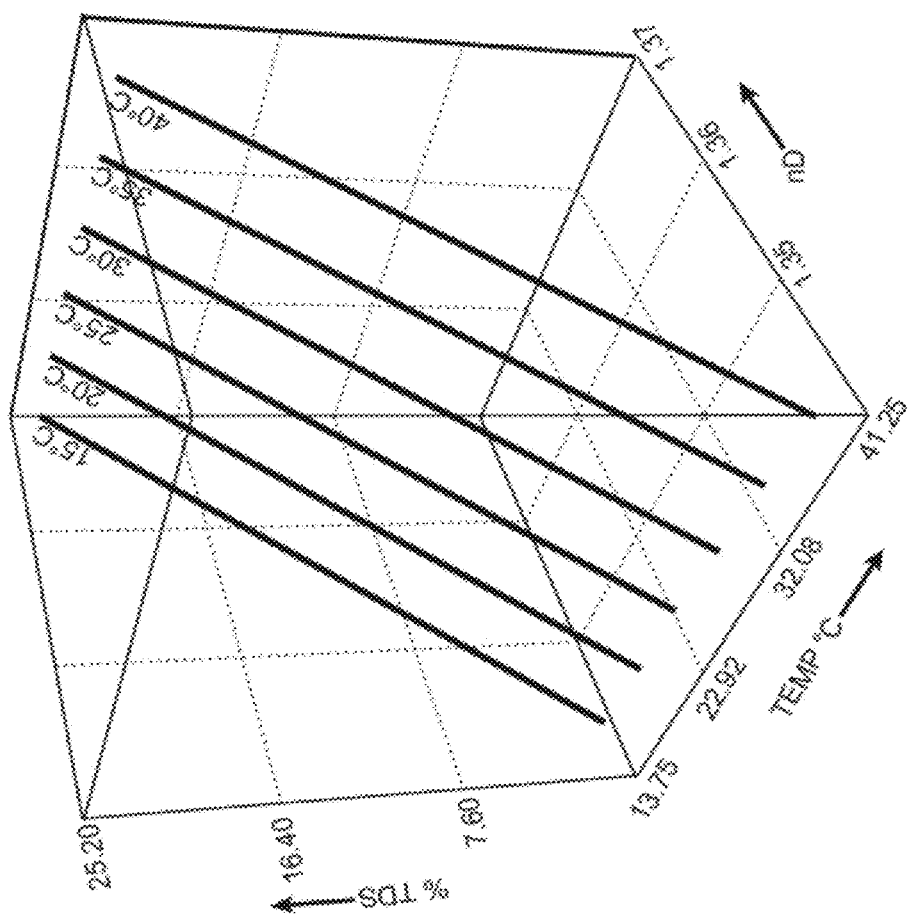
FIG. 15 is a scatter plot showing the 3 dimensional (3D) correlation of refractive index, temperature and concentration (% total dissolved solids) that the disclosed liquid design application employs.
Figure 16:
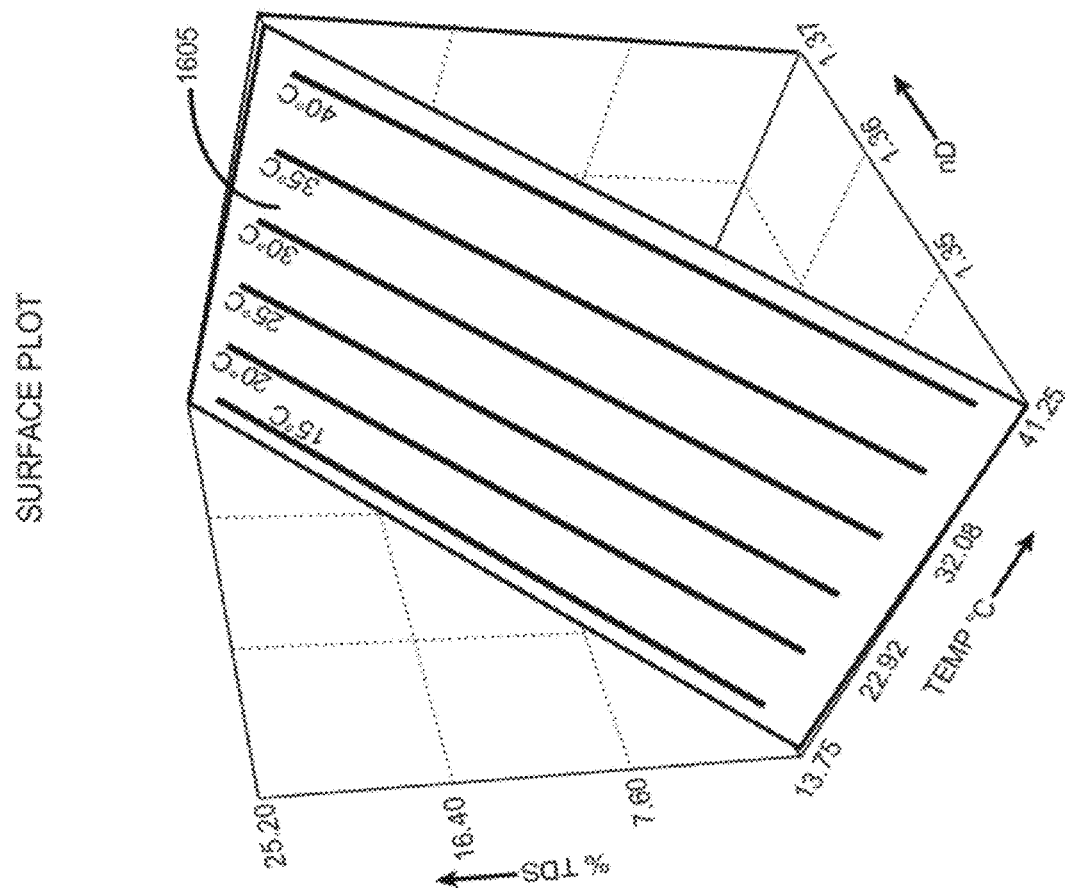
FIG. 16 is a surface plot showing the 3D correlation of refractive index, temperature and concentration (% total dissolved solids) that the disclosed liquid design application employs.
Figure 17:
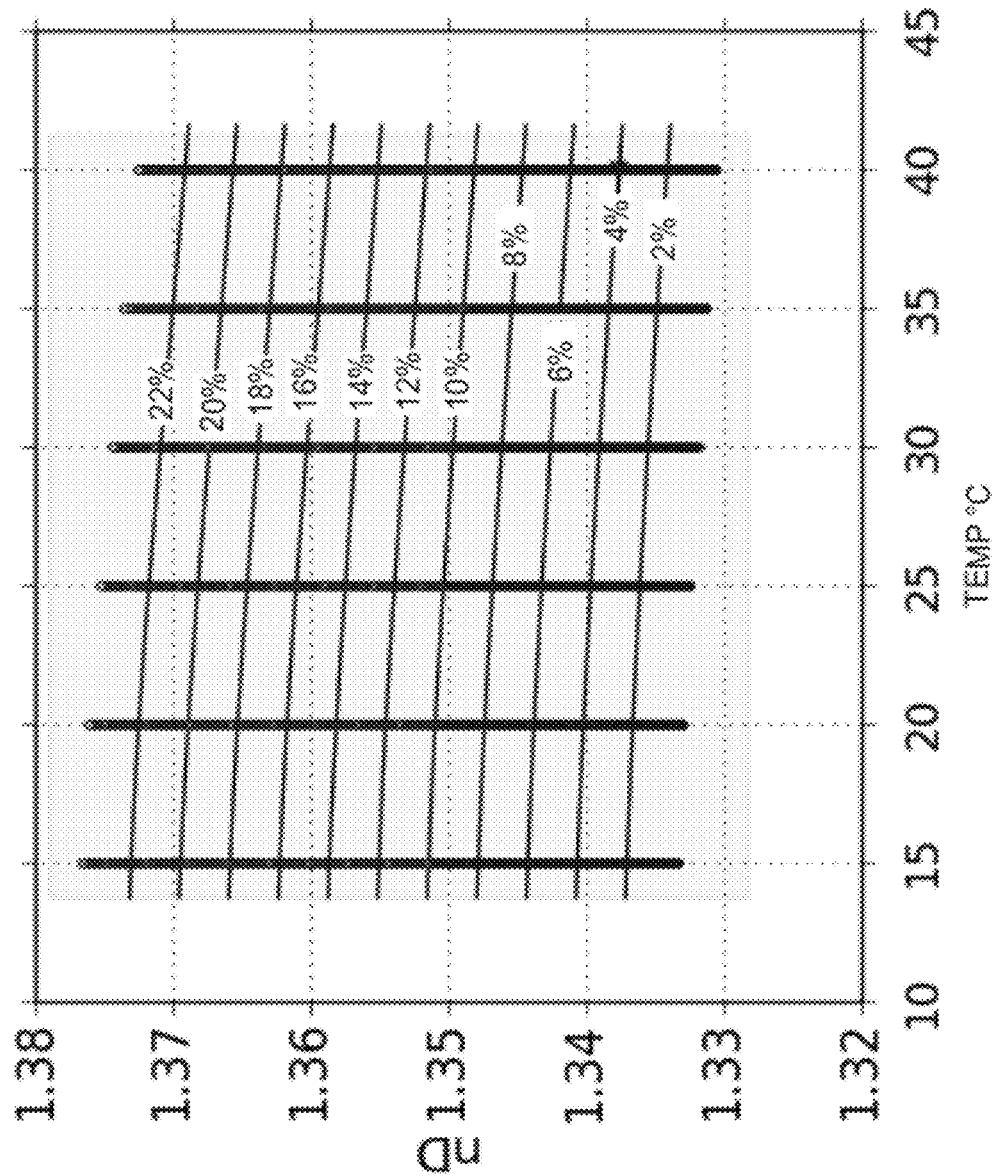
FIG. 17 is a contour plot showing the 3D correlation of refractive index, temperature and concentration (% total dissolved solids) that the disclosed liquid design application employs.

FIG. 15 is a representative 3 dimensional (3D) scatter plot of the raw data from TABLE 1 with temperature on the x axis, refractive index nD on the y axis and % TDS on the z axis. FIG. 16 is a 3 dimensional (3D) surface plot of the raw data from TABLE 1 with temperature on the x axis, refractive index nD on the y axis and % TDS on the z axis. The surface plot of FIG. 16 is similar to the scatter plot of FIG. 15, except with the plane of the temperature lines at 15° C., 20° C., 25° C., 30° C., 35° C., and 40° C. being filled in to form a continuous surface 1605. FIG. 17 is yet another 3D plot of the raw data of TABLE 1, namely a contour plot with temperature on the x axis, refractive index nD on the y axis and a respective concentration line for the following concentrations, 2% TDS, 4% TDS, 6% TDS . . . 22% TDS.

Liquid design application 105 employs an advanced 3D polynomial equation that fits the curve 1605 of the raw data that the surface plot of FIG. 16 represents. By advanced 3D polynomial equation is meant an equation that is a higher order than a 2D polynomial equation which correlates 2 variables. In other words, an advanced 3D polynomial equation is a polynomial equation that correlates 3 variables. In this manner, liquid design application 105 is able to determine concentration of the liquid under test over a wide range of temperatures and a wide range of concentrations without resorting to a separate scale to determine concentration for each temperature. One equation that produces acceptable results is the full quadratic equation given in TABLE 2 below. The advanced polynomial equation of TABLE 2 employs 6 coefficients.

TABLE 2

$$z = a + bx + cy + dx^2 + ey^2 + fxy$$

wherein
a = −7.27705E+02
b = −8.72678E−01
c = 5.46065E+02
d = 9.20185E−04
e = −4.68197E−01
f = 6.648126E−01 and
x = temp
y = nD
z = % TDS Liquid design application 105 uses curve fitting to select the coefficients a, b, c, d and e to match the curve of the surface plot 1605 of FIG. 16. For applications that may require greater accuracy, a higher order advanced polynomial equation may be used such as an equation in the form of TABLE 3 below. The advanced polynomial equation of TABLE 3 employs 16 coefficients. The number of coefficients and order of the equation can be selected according to the degree of accuracy desired for a particular application.

TABLE 3

$$z = a + bx^0y^1 + cx^0y^2 + dx^0y^3 + ex^1y^0 + fx^1y^1 + gx^1y^2 + hx^1y^3 + ix^2y^0 + jx^2y^1 + kx^2y^2 + lx^2y^3 + mx^3y^0 + nx^3y^1 + ox^3y^2 + px^3y^3$$

wherein
x = temp
y = nD
z = % TDS

In one embodiment, using an advanced polynomial equation such as those discussed above, liquid design application 105 is able to accurately determine % TDS concentration for a particular liquid at virtually all temperatures and virtually all concentrations of interest using a single SCALE 1 such as shown in FIG. 1, in one system, namely refractometer system 100 of FIG. 1 or portable liquid design system 200 of FIG. 2. The needs of an entire industry (e.g. the coffee industry) may be met in single device which employs SCALE 1 that employs a specific advanced polynomial equation. In one embodiment depicted in FIG. 1, the refractometer system 100 may employ not only a SCALE 1 that meets the needs of the coffee industry, but the same instrument may also include a SCALE 2 that meets the needs of another industry, for example, the espresso industry, the corn syrup industry, the sugar industry, the medical industry (blood analysis, urine analysis) and other industries. In that embodiment, SCALE 2 employs an advanced polynomial equation derived from raw data similar to TABLE 1 except for a different liquid type of interest, i.e. espresso, corn syrup and others. In that scenario, SCALE 2 is a scale that correlates all refractive indexes of interest, all temperatures of interest and all concentrations % TDS of interest. This embodiment includes one scale per substance under test.

Figure 18:
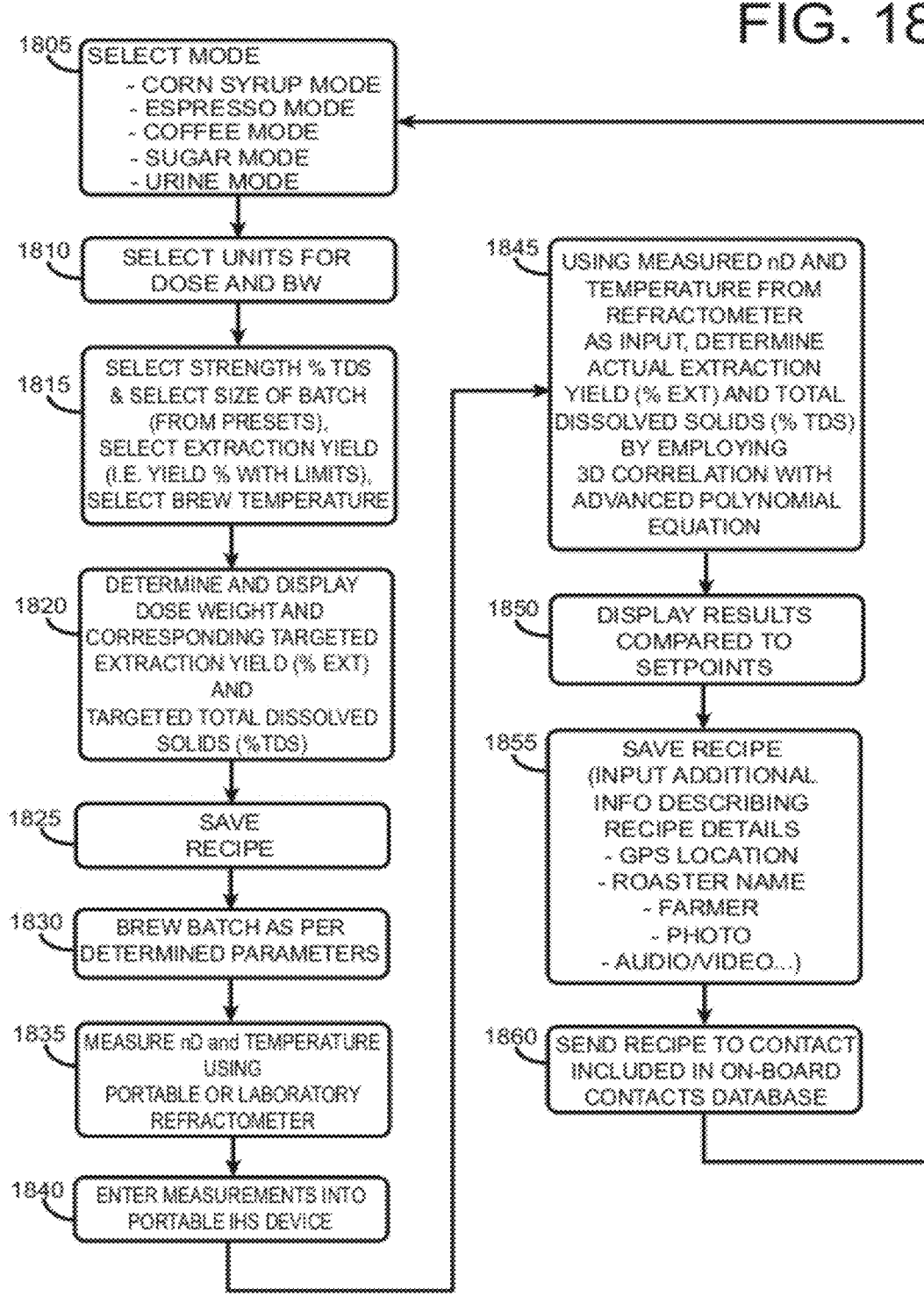
FIG. 18 a flowchart that shows representative process steps that the disclosed liquid design application employs.

FIG. 18 is a flowchart that illustrates the process steps that liquid design application 105 performs to carry out one embodiment of the disclosed methodology. The user selects a mode of liquid design application 105, for example corn syrup mode, espresso mode, coffee mode, sugar mode, urine mode, blood plasma mode as well as other modes, as per block 1805. Using application 105, the user may then select units for the dose and brew water (BW) amount, as per block 1810. The user also may select a strength of total dissolved solids (% TDS) and batch size by selecting from multiple presets if desired, as per block 1815. The user may also select an extraction yield within predetermined limits 721B and 721C (of FIG. 12A) that specify a range of interest. The user may also select the water start temperature in application 105.

Using the above parameters as input, liquid design application 105 determines and displays the dose weight and the corresponding targeted extraction yield (% EXT) and the targeted total dissolved solids (% TDS). The user may optionally instruct application 105 to save the current recipe at this point, as per block 1825. The user may now brew a batch of the liquid under test, e.g. coffee if in coffee mode, according to the above parameters, as per block 1830. The application can be set to mark this design recipe point, and then the actual measurements made using the nD and temperature, so that the user may see the measured versus the design values simultaneously on the displayed results. These parameters too are saved and transmitted when shared.

Once a batch of the liquid under test is brewed or mixed, liquid design application 105 may test the liquid to determine if it actually meets the parameters of the recipe, for example the extraction yield (% EXT) and total dissolved solids (% TDS) criteria. To do so, refractometer 100 of FIG. 1 or refractometer 235 of FIG. 2 measures the refractive index (nD or $n_s$) and temperature of the liquid sample, as per block 1835. Referring to FIG. 2, refractometer 235 transmits the refractive index and temperature of the liquid sample to portable IHS 205 as input information. Alternatively, the user may manually enter the refractive index and temperature information into portable IHS 205, as per block 1840.

Portable IHS 205 then uses the measured nD (or $n_s$) and sample temperature as input to the advanced polynomial equation, as per block 1845. From this information, portable IHS 205 uses the advanced polynomial equation to determine the actual extraction yield (% EXT) and total dissolved solids (% TDS) achieved when the user made the batch of coffee according to the recipe. As per block 1850, the user may consult display 275 to readily observe whether or not the concentration % EXT falls between the desired limits, set points or trigger points 721A and 721B as seen in FIG. 12. As explained above, should the actual extraction yield (% EXT) fall outside of the trigger points, the user can readily observe this condition on the display by both the location of the indicator bar outside the desired range and by a color alert cue that triggers when outside the desired range.

The user may instruct liquid design application 105 to save the current recipe, as per block 1855. The user may provide additional recipe details such as the GPS location of the brewing location, the roaster's name, the farm, and other information such as shown in FIGS. 13A-13F, by way of example. Liquid design application 105 may prompt the user to send the recipe via email to a contact included in an onboard contacts database within portable IHS 205, as per block 1860. Process flow then continues back to select mode block 1850 where the user may decide to select the same mode to work on the same type of liquid or another mode to begin work with another type of liquid.

Those skilled in the art will appreciate that the various structures disclosed can be implemented in hardware, embedded firmware or software, and maintained and maintained wirelessly over the Internet. Moreover, the methodology represented by the blocks of the flowcharts of FIG. 18 may be embodied in a computer program product, such as a media disk, media drive or other media storage such as computer program product medium 105 of FIG. 2.

In one embodiment, liquid design application 105 implements the disclosed methodology as a set of instructions (program code) in a code module which may, for example, reside in the system memory 215 of portable IHS 205 of FIG. 2. Until IHS 205 requires this set of instructions, another memory, for example, non-volatile storage 220 such as a hard disk drive, or a removable memory such as an optical disk or floppy disk, may store this set of instructions. IHS 205 may also download this set of instructions via the Internet or other computer network. Thus, a computer program product may implement the disclosed methodology for use in a computer such as IHS 205. In such a software embodiment, RAM or system memory 215 may store code that carries out the functions described in the flowchart of FIG. 18 while processor 210 executes such code. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the required method steps. In the context of this document, a computer program product or computer-readable medium may be any medium that can contain, store, communicate, propagate, or transport the program for use by or in connection with the instruction execution system, apparatus, or device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of designing a liquid under test, comprising:
providing, by a portable information handling system (IHS), at least one 3 dimensional (3D) polynomial scale of the correlation of refractive indexes, temperatures and concentrations of the liquid under test, the providing of the 3D polynomial scale being on a single 3D polynomial scale per liquid type basis;
measuring, by a refractometer, the refractive index and temperature of a liquid under test;
receiving, by the portable IHS, a refractive index measurement and temperature measurement from the refractometer for the liquid under test;
applying, by the portable IHS, the refractive index measurement and temperature measurement to the 3D polynomial scale to determine the corresponding concentration of the liquid under test; and
displaying, by the portable IHS, the corresponding concentration of the liquid under test.

2. The method of claim 1, further comprising displaying, by the portable IHS, a plurality of preset liquid under test strength values and a plurality of preset water size values for selection by a user.

3. The method of claim 2, further comprising switching units of measurement for the water size values from one type of unit of measurement to another type of unit of measurement in response to user input to the portable IHS.

4. The method of claim 1, further comprising receiving, by the portable IHS, a user selection that indicates a predetermined lower percent extraction trigger point value and a predetermined upper percent extraction trigger point value to specify a region of interest.

5. The method of claim 4, further comprising displaying, by the portable IHS, a first predetermined cue color if actual % extraction is less than the predetermined lower percent extraction trigger point value and displaying a second predetermined cue color if the actual percent extraction is more than the predetermined upper percent extraction point value.

6. The method of claim 1, further comprising storing, by the portable IHS, a plurality of 3 dimensional (3D) polynomial scales of the correlation of refractive indexes, temperatures and concentrations of respective liquids under test, each scale corresponding to a different single 3D polynomial on a per liquid type basis.

7. A method of designing a liquid under test, comprising:
providing, by a refractometer, at least one 3 dimensional (3D) polynomial scale of the correlation of refractive indexes, temperatures and concentrations of the liquid under test, the providing of the 3D polynomial scale being on a single 3D polynomial scale per liquid type basis;
measuring, by the refractometer, the refractive index and temperature of a liquid under test;
receiving, by a liquid design application in the refractometer, a refractive index measurement and temperature measurement for the liquid under test;
applying, by the liquid design application, the refractive index measurement and temperature measurement to the 3D dimensional polynomial scale to determine the corresponding concentration of the liquid under test; and
displaying, by a display of the refractometer, the corresponding concentration of the liquid under test.

8. The method of claim 7, further comprising displaying, by the display, a plurality of preset liquid under test strength values and a plurality of preset water size values for selection by a user.

9. The method of claim 8, further comprising switching units of measurement for the water size values from one type of unit of measurement to another type of unit of measurement in response to user input to the refractometer.

10. The method of claim 7, further comprising receiving, by the refractometer, a user selection that indicates a predetermined lower percent extraction trigger point value and a predetermined upper percent extraction trigger point value to specify a region of interest.

11. The method of claim 10, further comprising displaying, by the display, a first predetermined cue color if actual percent extraction is less than the predetermined lower percent extraction trigger point value and displaying a second predetermined cue color if the actual % extraction is more than the predetermined upper percent extraction point value.

12. The method of claim 7, further comprising storing, by the refractometer, a plurality of 3 dimensional (3D) polynomial scales of the correlation of refractive indexes, temperatures and concentrations of respective liquids under test, each scale corresponding to a different single 3D polynomial on a per liquid type basis.

13. A liquid design system for use on a liquid under test, comprising:
a processor;
a display coupled to the processor;
a memory coupled to the processor, the memory being configured with a liquid design application that:
provides at least one 3 dimensional (3D) polynomial scale of the correlation of refractive indexes, temperatures and concentrations of the liquid under test, the providing of the 3D polynomial scale being on a single 3D polynomial scale per liquid type basis;
receives, from a refractometer, a refractive index measurement and a temperature measurement for the liquid under test;
applies the refractive index measurement and temperature measurement to the 3D polynomial scale to determine the corresponding concentration of the liquid under test; and
displays the corresponding concentration of the liquid under test.

14. The liquid design system of claim 13, wherein the display displays a plurality of preset liquid under test strength values and a plurality of preset water size values for selection by a user.

15. The liquid design system of claim 14, wherein the liquid design application switches units of measurement for the water size values from one type of unit of measurement to another type of unit of measurement in response to user input to the liquid design system.

16. The liquid design system of claim 13, wherein the liquid design system receives a user selection that indicates a predetermined lower percent extraction trigger point value and a predetermined upper percent extraction trigger point value to specify a region of interest.

17. The liquid design system of claim 16, wherein the display of the liquid design system displays a first predetermined cue color if actual percent extraction is less than the predetermined lower percent extraction trigger point value and displays a second predetermined cue color if the actual percent extraction is more than the predetermined upper % extraction point value.

18. The liquid design system of claim 13, wherein the memory store stores a plurality of 3 dimensional (3D) polynomial scales of the correlation of refractive indexes, temperatures and concentrations of respective liquids under test, each scale corresponding to a different single 3D polynomial on a per liquid type basis.

19. A liquid design system for use on a liquid under test, comprising:
a processor;
a display coupled to the processor;
a memory store situated in the processor, the memory store being embedded with a liquid design application that:
provides at least one 3 dimensional (3D) polynomial scale of the correlation of refractive indexes, temperatures and concentrations of the liquid under test, the providing of the 3D polynomial scale being on a single 3D polynomial scale per liquid type basis;
receives, from a refractometer, a refractive index measurement and a temperature measurement for the liquid under test;
applies the refractive index measurement and temperature measurement to the 3D polynomial scale to determine the corresponding concentration of the liquid under test; and
displays the corresponding concentration of the liquid under test.

20. The liquid design system of claim 19, wherein the display displays a plurality of preset liquid under test strength values and a plurality of preset water size values for selection by a user.

21. The liquid design system of claim 20, wherein the liquid design application switches units of measurement for the water size values from one type of unit of measurement to another type of unit of measurement in response to user input to the refractometer.

22. The liquid design system of claim 19, further comprising receiving, by the refractometer, a user selection that indicates a predetermined lower percent extraction trigger point value and a predetermined upper percent extraction trigger point value to specify a region of interest.

23. The liquid design system of claim 22, wherein the display of the liquid design system display a first predetermined cue color if actual percent extraction is less than the predetermined lower percent extraction trigger point value and displays a second predetermined cue color if the actual % extraction is more than the predetermined upper percent extraction point value.

24. The liquid design system of claim 19, wherein the memory store stores a plurality of 3 dimensional (3D) polynomial scales of the correlation of refractive indexes, temperatures and concentrations of respective liquids under test, each scale corresponding to a different single 3D polynomial on a per liquid type basis.

25. A computer program product comprising:
a nontransitory computer readable storage medium including a liquid design application;
first instructions that provide at least one 3 dimensional (3D) polynomial scale of the correlation of refractive indexes, temperatures and concentrations of the liquid under test, the providing of the 3D polynomial scale being on a single 3D polynomial scale per liquid type basis;
second instructions that receive, from a refractometer, a refractive index measurement and a temperature measurement for the liquid under test;
third instructions that apply the refractive index measurement and temperature measurement to the 3D polynomial scale to determine the corresponding concentration of the liquid under test; and
fourth instructions that display the corresponding concentration of the liquid under test;
wherein the first, second, third and fourth instructions are stored on the computer readable storage medium.

* * * * *